(12) United States Patent
Kamatani et al.

(10) Patent No.: US 9,590,199 B2
(45) Date of Patent: Mar. 7, 2017

(54) ORGANIC COMPOUND, ORGANIC LIGHT EMITTING DEVICE, AND IMAGE DISPLAY DEVICE

(71) Applicant: CANON KABUSHIKI KAISHA, Tokyo (JP)

(72) Inventors: Jun Kamatani, Tokyo (JP); Shigemoto Abe, Yokohama (JP); Masashi Hashimoto, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 343 days.

(21) Appl. No.: 14/363,063

(22) PCT Filed: Nov. 26, 2012

(86) PCT No.: PCT/JP2012/081220
§ 371 (c)(1),
(2) Date: Jun. 5, 2014

(87) PCT Pub. No.: WO2013/084833
PCT Pub. Date: Jun. 13, 2013

(65) Prior Publication Data
US 2014/0374723 A1  Dec. 25, 2014

(30) Foreign Application Priority Data

Dec. 6, 2011 (JP) ................................ 2011-267142
Oct. 19, 2012 (JP) ................................ 2012-232175

(51) Int. Cl.
*H01L 51/50* (2006.01)
*H01L 51/00* (2006.01)
(Continued)

(52) U.S. Cl.
CPC ............ *H01L 51/504* (2013.01); *C07C 13/62* (2013.01); *C07C 25/22* (2013.01); *C07C 43/21* (2013.01);
(Continued)

(58) Field of Classification Search
CPC ... C07C 13/62; C07C 2103/54; C07C 211/61; C07C 255/52; C07C 25/22;
(Continued)

(56) References Cited

U.S. PATENT DOCUMENTS 7,368,624 B2 * 5/2008 Brown ..................... C07C 2/82
585/422
2002/0168544 A1 * 11/2002 Fukuoka ................. C09K 11/06
428/690

(Continued)

FOREIGN PATENT DOCUMENTS

EP      2054360 B1    11/2010
JP      H11-040360 A   2/1999
(Continued)

OTHER PUBLICATIONS

Alexander McKillop et al, Thallium in Organic Synthyesis 58. Regiospecific Intermolecular Oxidative Dehydrodimerization of Aromatic Compounds to Biaryls Using Thallium (III) Trifluoroacetate, J.Am.Chem.Soc.,1980, 102, pp. 6504-6512.

(Continued)

*Primary Examiner* — Dawn Garrett
(74) *Attorney, Agent, or Firm* — Canon U.S.A. Inc., IP Division

(57) ABSTRACT

To provide a novel organic compound suitable for an organic light emitting device. This invention provides an organic compound having the skeleton represented by Formula (1).

(Continued)

(1)

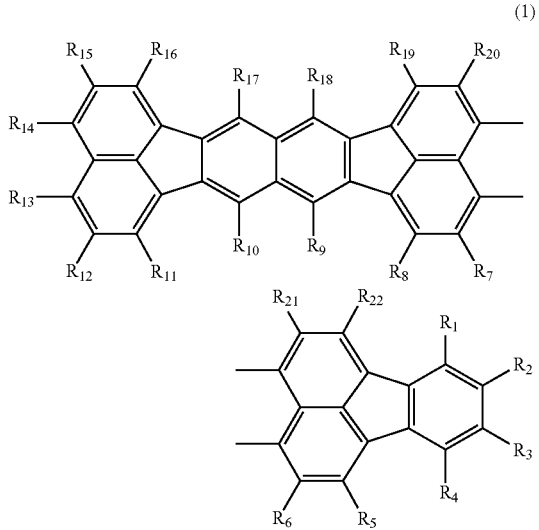

17 Claims, 1 Drawing Sheet

(51) Int. Cl.
| | |
|---|---|
| H01L 27/32 | (2006.01) |
| C07C 211/61 | (2006.01) |
| C07C 13/62 | (2006.01) |
| C07C 25/22 | (2006.01) |
| C09K 11/06 | (2006.01) |
| C07C 255/52 | (2006.01) |
| C07D 333/54 | (2006.01) |
| C07D 333/76 | (2006.01) |
| C07D 251/24 | (2006.01) |
| C07D 209/86 | (2006.01) |
| C07D 213/06 | (2006.01) |
| C07C 43/21 | (2006.01) |
| C07C 43/23 | (2006.01) |
| C07D 213/53 | (2006.01) |
| H05B 33/10 | (2006.01) |
| C09B 57/00 | (2006.01) |
| C09B 3/14 | (2006.01) |

(52) U.S. Cl.
CPC ............ *C07C 43/23* (2013.01); *C07C 211/61* (2013.01); *C07C 255/52* (2013.01); *C07D 209/86* (2013.01); *C07D 213/06* (2013.01); *C07D 213/53* (2013.01); *C07D 251/24* (2013.01); *C07D 333/54* (2013.01); *C07D 333/76* (2013.01); *C09B 3/14* (2013.01); *C09B 57/00* (2013.01); *C09K 11/06* (2013.01); *H01L 27/322* (2013.01); *H01L 27/3244* (2013.01); *H01L 51/006* (2013.01); *H01L 51/0056* (2013.01); *H05B 33/10* (2013.01); *C07C 2103/54* (2013.01); *C09K 2211/1007* (2013.01); *C09K 2211/1011* (2013.01); *H01L 51/5028* (2013.01)

(58) Field of Classification Search
CPC ....... C07C 43/21; C07C 43/23; C07D 209/86; C07D 213/06; C07D 213/53; C07D 251/24; C07D 333/54; C07D 333/76; C09B 3/14; C09B 57/00; C09K 11/06; C09K 2211/1007; C09K 2211/1011; H01L 27/322; H01L 27/3244; H01L 51/0056; H01L 51/006; H01L 51/5028; H01L 51/504; H05B 33/10
See application file for complete search history.

(56) References Cited

U.S. PATENT DOCUMENTS

| | | | |
|---|---|---|---|
| 2003/0161368 A1* | 8/2003 | Kahen | B23K 11/255 372/39 |
| 2007/0104977 A1* | 5/2007 | Arakane | H01L 51/0072 428/690 |
| 2008/0007160 A1* | 1/2008 | Sado | C09K 11/06 313/504 |
| 2009/0033218 A1 | 2/2009 | Ikeda | |
| 2013/0056722 A1* | 3/2013 | Nishide | C07C 13/62 257/40 |
| 2013/0174910 A1* | 7/2013 | Yasukawa | C07C 211/61 136/263 |

FOREIGN PATENT DOCUMENTS

| | | |
|---|---|---|
| JP | 2001-288126 A | 10/2001 |
| JP | 2002-110354 A | 4/2002 |
| JP | 2003-040815 A | 2/2003 |
| JP | 2007-520060 A | 7/2007 |
| JP | 2010-143880 A | 7/2010 |
| JP | 2012-144459 A | 8/2012 |
| RU | 2422425 C1 | 6/2011 |
| RU | 2434836 C2 | 11/2011 |
| WO | 01/23497 A1 | 4/2001 |
| WO | 2007/099802 A1 | 9/2007 |
| WO | 2010/071223 A1 | 6/2010 |

OTHER PUBLICATIONS

Jeff D. Debad, et al., Dibenzotetraphenylperiflanthene: Synthesis, Photophysical Properties, and Electrogenerated Chemiluminescence, J.Am.Chem.Soc., 1996, 118, pp. 2374-2379.

* cited by examiner

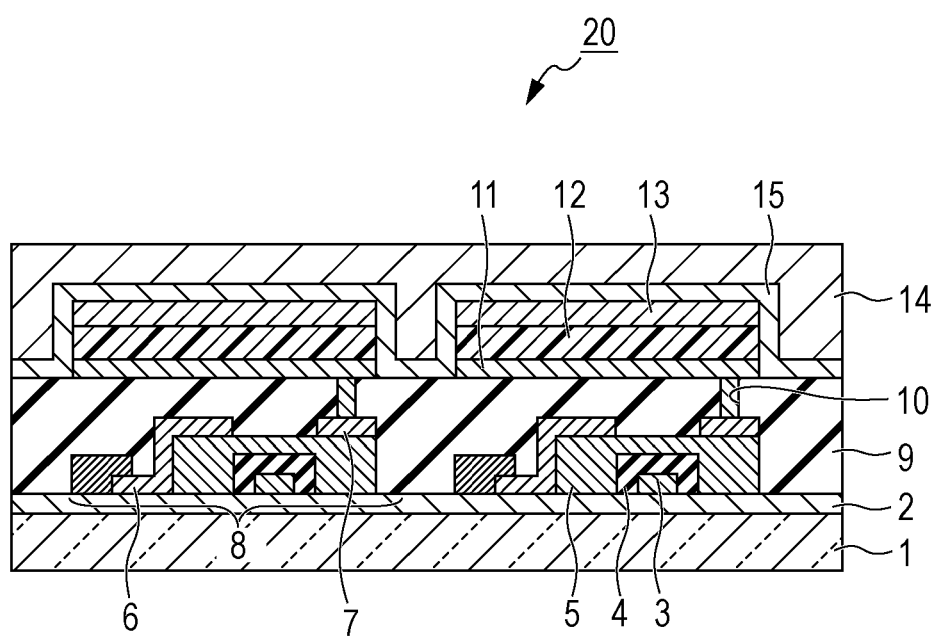

ORGANIC COMPOUND, ORGANIC LIGHT EMITTING DEVICE, AND IMAGE DISPLAY DEVICE

TECHNICAL FIELD

The present invention relates to a novel organic compound and an organic light emitting device and an image display device having the same.

BACKGROUND ART

An organic light emitting device (referred to as an organic electroluminescent device or an organic EL device) is an electronic device having a pair of electrodes and an organic compound layer disposed between these electrodes. By injecting electrons and holes from the pair of electrodes, an exciton of a luminescent organic compound in the organic compound layer is generated. Then, when the exciton returns to the ground state, the organic light emitting device emits light.

Recent progress of the organic light emitting device is remarkable. For example, a low drive voltage, various light emission wavelengths, high-speed responsiveness, and a reduction in thickness and weight of a light emitting device can be achieved.

The creation of the luminescent organic compound has been actively performed so far. This is because, in providing a highly efficient organic light emitting device, the creation of compounds having excellent luminescent properties is important.

As the compounds which were created so far, the following compound 1-A disclosed in PTL 1 and the following compound 1-B disclosed in PTL 2 are mentioned, for example.

[Chem. 1]

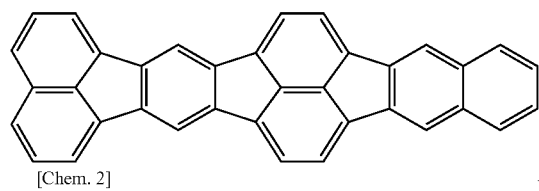

1-A

[Chem. 2]

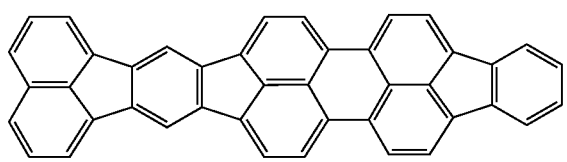

1-B

According to the investigation of the present inventors, the compound 1-A emits yellow light and hardly emits light as described later.

According to the investigation of the present inventors, the compound 1-B emits red light and hardly emits light as described later.

CITATION LIST

Patent Literature

PTL 1 Japanese Patent Laid-Open No. 2002-110354
PTL 2 Japanese Patent Laid-Open No. 2001-288126

SUMMARY OF INVENTION

Technical Problem

However, the basic skeleton of the compound described in PTL 1 or PTL 2 does not achieve light emission with a high quantum yield as described above.

The invention provides an organic compound which emits light in a red region. The present invention also provides an organic light emitting device with high luminous efficiency.

Therefore, the invention provides an organic compound represented by the following general formula (1):

[Chem. 3]

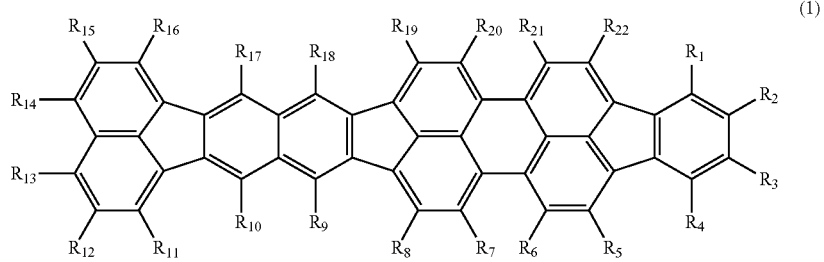

(1)

in which, in Formula (1), $R_1$ to $R_{22}$ each are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted arylocxy group, a silyl group, and a cyano group.

BRIEF DESCRIPTION OF DRAWINGS

FIG. 1 is a cross-sectional schematic view illustrating an example of a display device having an organic light emitting device of the invention and a transistor electrically connected to the organic light emitting device.

DESCRIPTION OF EMBODIMENTS

First, an organic compound according to the invention is described. A novel organic compound according to the invention is an organic compound having a basic skeleton represented by the following Formula (1).

[Chem. 4]

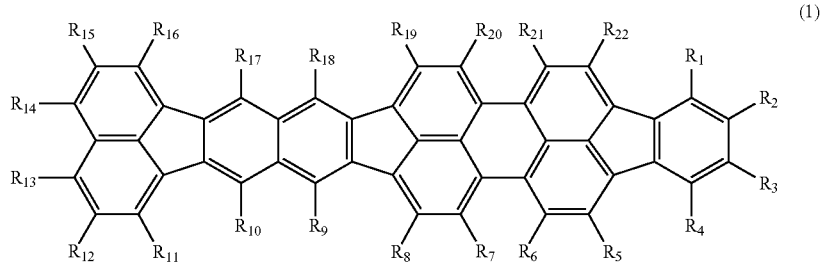

(1)

In Formula (1), $R_1$ to $R_{22}$ each shown in the basic skeleton are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted arylocxy group, a silyl group, and a cyano group.

In this embodiment, $R_1$ to $R_{22}$ in Formula (1) each are suitably independently selected from a hydrogen atom, a substituted or unsubstituted alkyl group, and a substituted or unsubstituted aryl group.

Mentioned as the halogen atom represented by $R_1$ to $R_{22}$ are fluoride, chlorine, bromine, iodine, and the like but the halogen atom is not limited thereto.

Mentioned as the alkyl group represented by $R_1$ to $R_{22}$ are a methyl group, an ethyl group, a normal propyl group, an isopropyl group, a normal butyl group, a tertiary butyl group, a secondary butyl group, an octyl group, a cyclohexyl group, a 1-adamantyl group, a 2-adamantyl group, and the like but the alkyl group is not limited thereto.

Mentioned as the alkoxy group represented by $R_1$ to $R_{22}$ are a methoxy group, an ethoxy group, a propoxy group, a 2-ethyl-octyloxy group, a benzyloxy group, and the like but the alkoxy group is not limited thereto.

Mentioned as the amino group represented by $R_1$ to $R_{22}$ are an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary-butylphenyl)amino group, an N-phenyl-N-(4-trifluoromethylphenyl)amino group, and an N-piperidyl group, and the like but the amino group is not limited thereto.

Mentioned as the aryl group represented by $R_1$ to $R_{22}$ are a phenyl group, a naphthyl group, an indenyl group, a biphenyl group, a terphenyl group, a fluorenyl group, and the like but the aryl group is not limited thereto.

Mentioned as the heterocyclic group represented by $R_1$ to $R_{22}$ are a pyridyl group, an oxazolyl group, an oxadiazolyl group, a thiazolyl group, a thiadiazolyl group, a carbazolyl group, an acridinyl group, and a phenanthrolyl group, and the like but the heterocyclic group is not limited thereto.

Mentioned as the aryloxy group represented by $R_1$ to $R_{22}$ are a phenoxy group, a thienyloxy group, and the like but the aryloxy group is not limited thereto.

Mentioned as the silyl group represented by $R_1$ to $R_{22}$ are a triphenylsilyl group and the like but the silyl group is not limited thereto.

Mentioned as a substituent which the alkyl group, the alkoxy group, the amino group, the aryl group, the heterocyclic group, and the aryloxy group mentioned above may have are alkyl groups, such as a methyl group, an ethyl group, a normal propyl group, an isopropyl group, a normal butyl group, and a tertiary butyl group, aralkyl groups, such as a benzyl group, aryl groups, such as a phenyl group and a biphenyl group, heterocyclic groups, such as a pyridyl group and a pyrrolyl group, amino groups, such as a dimethylamino group, a diethylamino group, a dibenzylamino group, a diphenylamino group, and a ditolylamino group, alkoxy groups, such as a methoxy group, an ethoxy group, and a propoxy group, aryloxy groups, such as a phenoxy group, halogen atoms, such as fluorine, chlorine, bromine, and iodine, a cyano group, and the like but the substituent is not limited thereto.

In this embodiment, $R_1$ to $R_{22}$ in Formula (1) each are suitably independently selected from a hydrogen atom and a substituted or unsubstituted aryl group.

The basic skeleton as used herein is a skeleton in which all of $R_1$ to $R_{22}$ of the compound represented by the following general formula (1) are replaced by a hydrogen atom.

When a substituent is introduced into the basic skeleton in the organic compound according to this embodiment, a compound can be obtained in which the concentration quenching is suppressed, the sublimation properties are improved in sublimation, and the solvent solubility is improved when used in application.

It is suitable from the viewpoint of the suppression of the concentration quenching that at least any one of $R_1$ to $R_{22}$ in Formula (1) is replaced by an alkyl group.

Next, a method for synthesizing the organic compound according to this embodiment is described. The organic compound according to this embodiment is synthesized according to the reaction scheme shown below, for example.

[Chem. 5]

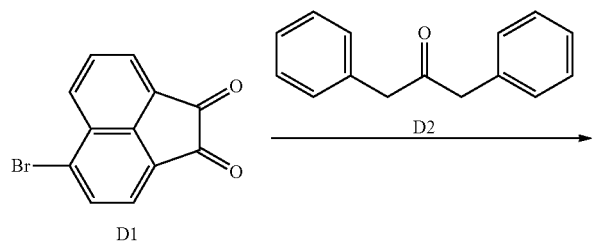

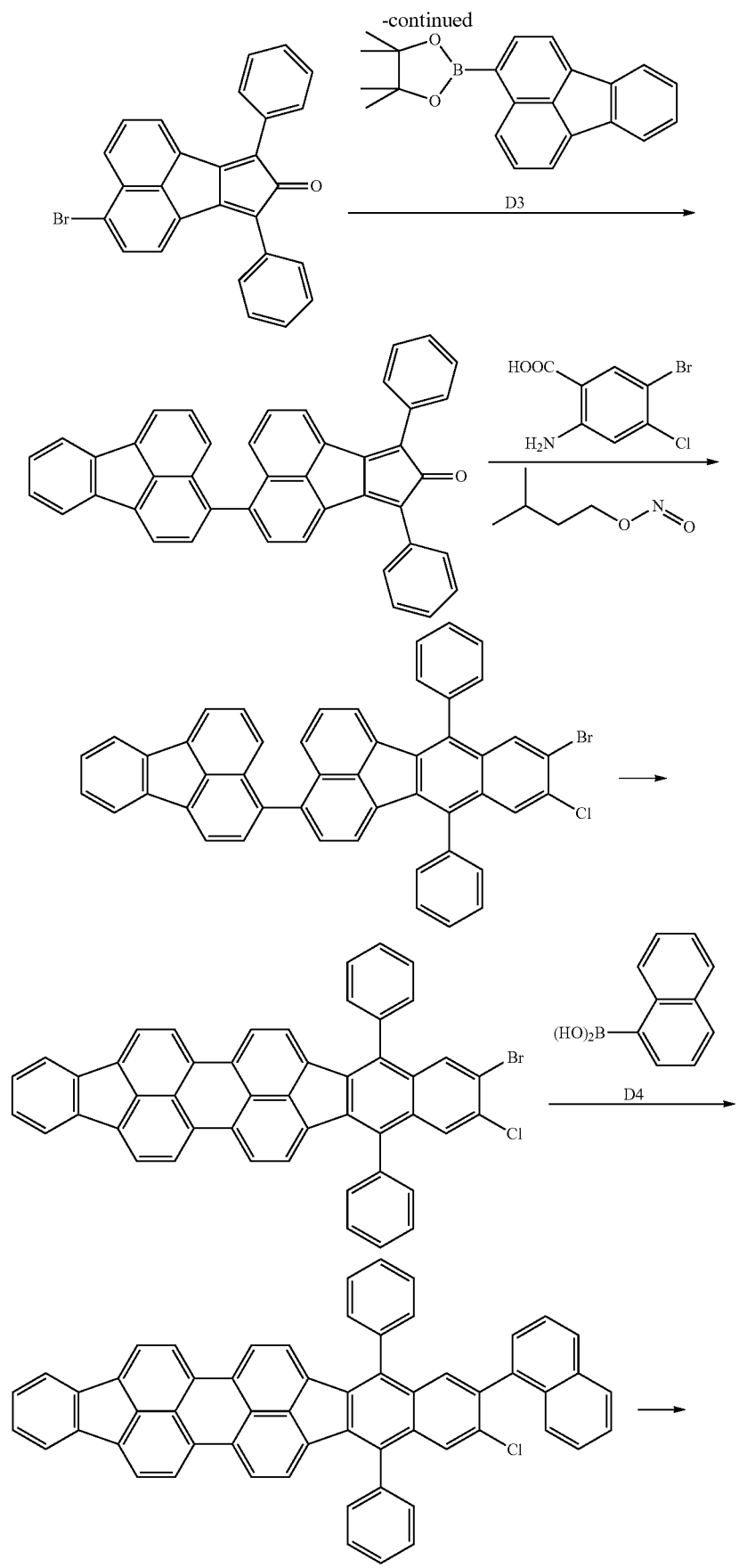

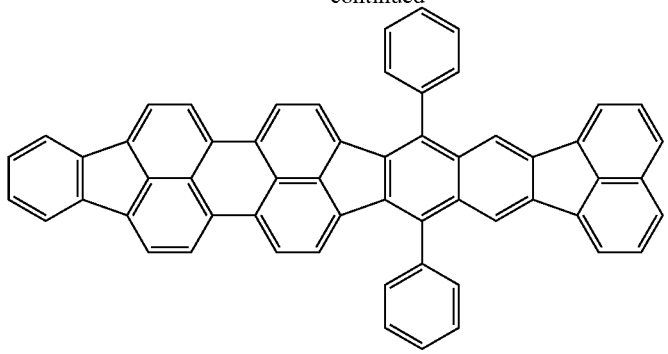

As represented by the synthetic scheme above, the organic compound according to this embodiment is synthesized using the compounds (a) to (d) shown below as the raw materials.
(a) Acenaphthenequinone derivative (D1)
(b) Dibenzylketone derivative (D2)
(c) Fluoranthene derivative (D3)
(d) Naphthalene derivative (D4)

Herein, by introducing a substituent into the compounds (a) to (d) above as appropriate, the hydrogen atom is replaced by a predetermined substituent in any one of $R_1$ to $R_{22}$ in Formula (1). Mentioned as the substituent to be introduced herein are an alkyl group, a halogen atom, a phenyl group, a methoxy group, a cyano group, and the like.

By individually changing D1 to D4 in the synthetic schemes above, various organic compounds can be synthesized.

Next, the characteristics of the basic skeleton of the organic compound according to this embodiment are described.

When the present inventors devise the organic compound represented by Formula (1), the present inventors have focused on the basic skeleton itself. Specifically, the present inventors have attempted to provide one in which the light emission wavelength of the molecules of only the basic skeleton is in a desired light emission wavelength region.

In this embodiment, the desired light emission wavelength region is a red region, and specifically the maximum light emission wavelength in a diluted solution is within a bandwidth of 580 nm or more and 620 nm or lower.

Next, the properties of the basic skeleton of the organic compound according to the invention are described while comparing comparative compounds having structures similar to that of the organic compound of the invention. Specifically, the compounds represented by the following formulae (2) and (3) are mentioned as the compounds to be compared.

[Chem. 6]

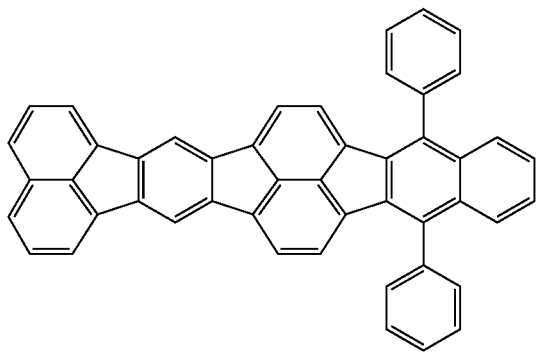

(2)

[Chem. 7]

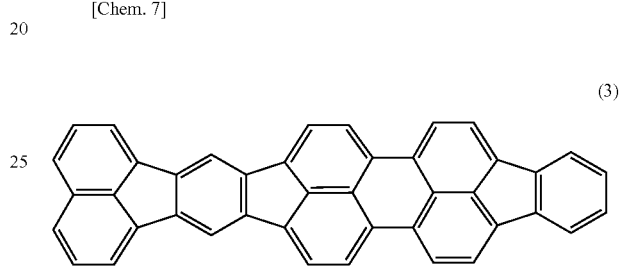

(3)

Herein, one of the organic compounds according to the invention has the basic skeleton represented by Formula (1) and is a compound represented by the following Formula (4) in which $R_1$ to $R_8$, $R_{10}$ to $R_{17}$, and $R_{19}$ to $R_{22}$ are hydrogen atoms and $R_9$ and $R_{18}$ are phenyl groups.

[Chem. 8]

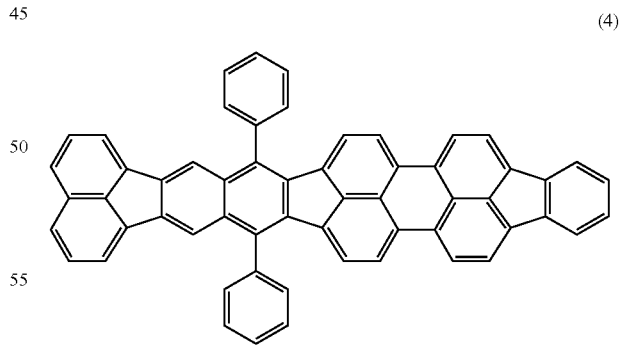

(4)

Herein, the preset inventors compared the light emission wavelength and the quantum yield in a toluene diluted solution of the organic compound represented by Formula (4) and the organic compounds represented by Formulae (2) and (3). The results are shown in Table 1.

TABLE 1

| Compound No. | Structural Formula | Maximum light emission wavelength (nm) | Quantum yield |
|---|---|---|---|
| 2 | 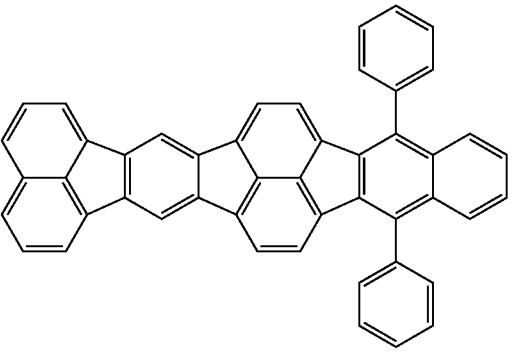 | 555 | <0.1 |
| 3 | 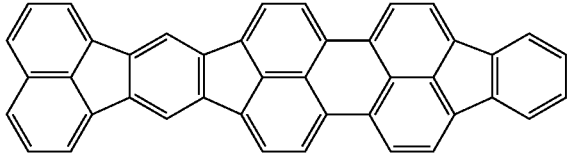 | 630 | <0.1 |
| 4 | 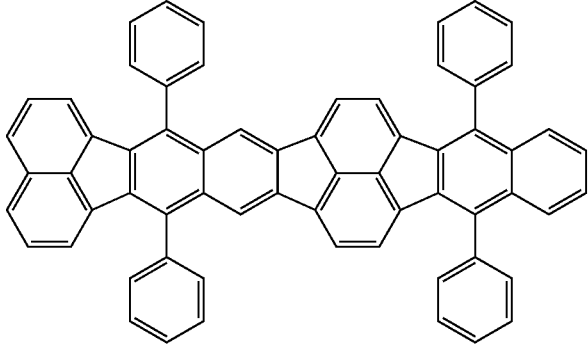 | 597 | 0.77 |

The light color of the compound 3 of Table 1 is yellow and is not red. The quantum yield thereof is 0.1 or lower, which is 10 or more times lower than that of the compound 4. This means that the energy produced when holes and electrons are recombined cannot be efficiently converted.

The light color of the compound 2 of Table 1 is yellow and is not red. The quantum yield thereof is 0.1 or lower, which is 10 or more times lower than that of the compound 4. This means that the energy produced when holes and electrons are recombined cannot be efficiently converted.

The compound 4 of Table 1 which is the compound of this embodiment has a higher quantum yield than that of the other materials and has a light color suitable for red color of the standard of a display. The half width of the waveform of the maximum light emission wavelength of the organic compound having this basic skeleton is 30 nm or lower. In contrast, the half width of the waveform of the maximum light emission wavelength of the organic compounds 2 and 3 is 50 nm or more. A difference in the half width is related to the color purity of the light color. When the half width is narrower, the color purity is high and when the half width is wide, the color purity decreases. In this respect, the basic skeleton of the invention can emit light with high purity to a demanded color and exhibits excellent properties. Moreover, the compound is a material having a quantum yield as high as 0.7 or more. Therefore, it can be said that the skeleton is excellent as a light emitting material of red color which can contribute to a reduction in the power consumption of an organic light emitting device.

Moreover, the organic compound according to this embodiment can suppress the crystallinity of the molecules themselves to some extent by further introducing a substituent. The suppression of crystallinity leads to control of the concentration quenching between molecules or improvement of sublimation properties. Specifically, in the case of an alkyl group, a methyl group, an ethyl group, a propyl group, a butyl group, a hexyl group, an octyl group, and the like are suitable, and particularly an isopropyl group or a tertiary butyl group which is three dimensionally large is suitable. Also in the case of an aryl group, an aryl group, such as a phenyl group having substituents, such as a methyl group, a xylyl group, a mesityl group, an isopropyl group, and a tertiary butylphenyl group, is suitable. Moreover, fluorine is also suitable in this respect. Moreover, since the film properties are improved when using the same for a method including compounding the same in liquid to dispose (apply) the same at a predetermined position, and then removing a solvent thereafter, it is suitable to introduce a substituent.

The position of the substituent is not particularly limited. The organic compound according to the invention has high planarity and excimer generation by stacking between molecules is likely to occur when not replaced. Therefore, the excimer generation needs to be suppressed. The position of the substituent at which the excimer generation is effectively suppressed is any one of the positions of $R_1$, $R_4$, $R_9$, $R_{10}$, $R_{17}$, and $R_{18}$ at which the substituent is likely to be orthogonal to the basic skeleton. Therefore, it is suitable to introduce a substituent, such as an aryl group or an alkyl group, to the position.

Since the organic compound according to this embodiment has three 5-membered ring structures in the skeleton, the LUMO energy level is low. This means that the oxidation potential of the compound is low. Therefore, the organic compound according to this embodiment is stable to oxidization.

The basic skeleton of the organic compound according to this embodiment is constituted by only carbon and does not have a hetero atom, such as a nitrogen atom. This also contributes to the fact that the oxidation potential of the compound itself is low and is one of the reasons why the organic compound according to this embodiment is stable to oxidization.

Specific examples of the organic compound according to the invention are shown below. However, the invention is not limited thereto.

[Chem. 9]

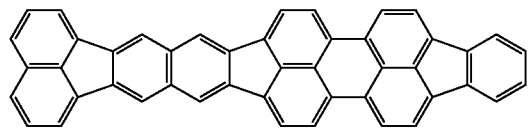

A1

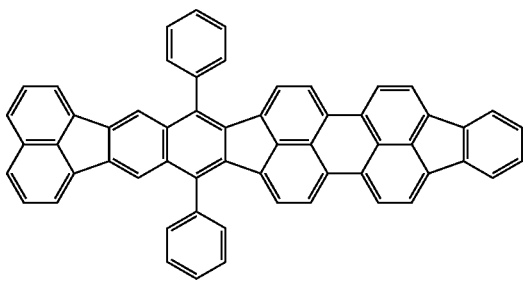

A2

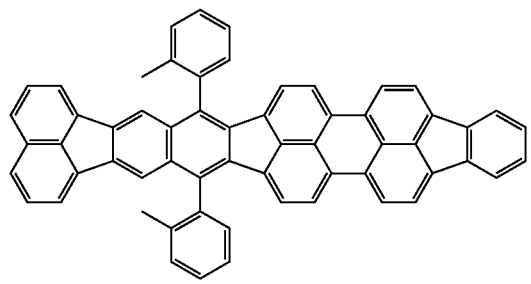

A3

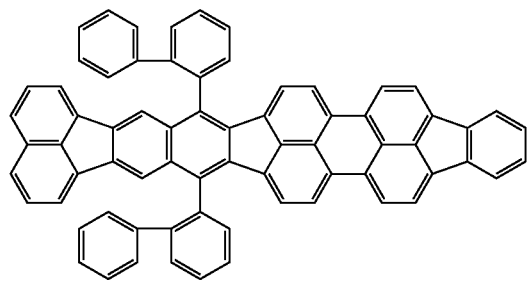

A5

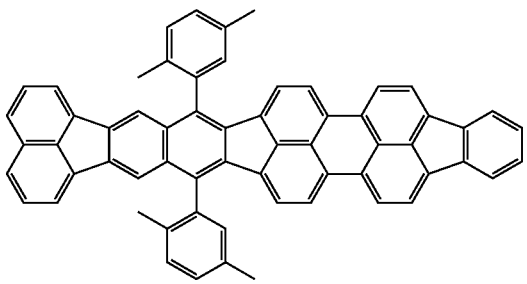

A4

A6

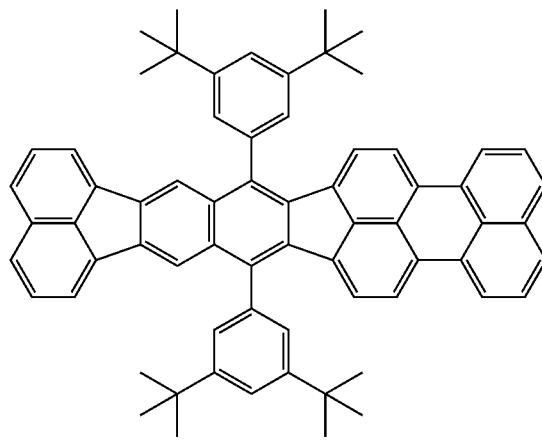

A7

-continued
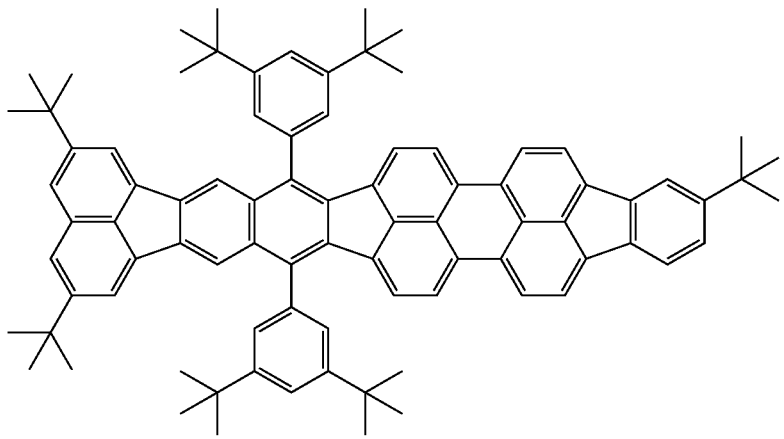
A8
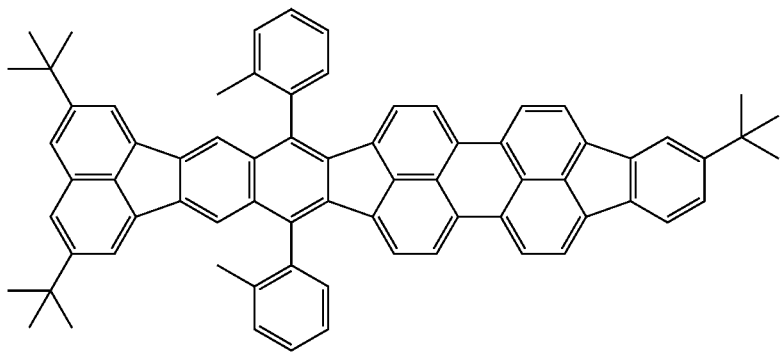
A9
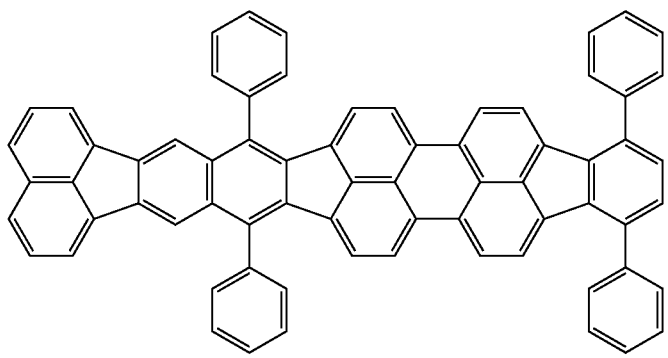
A10
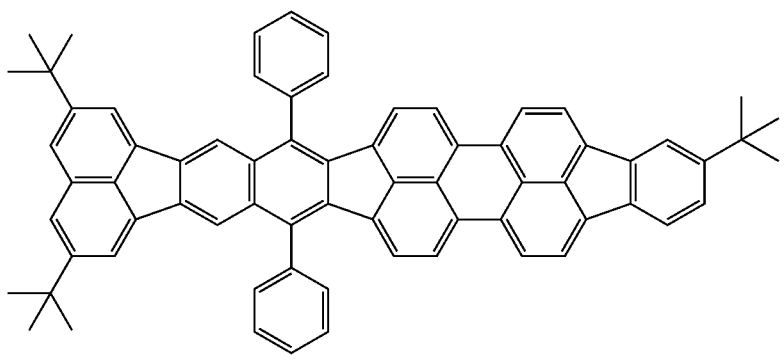
A11

-continued
A12
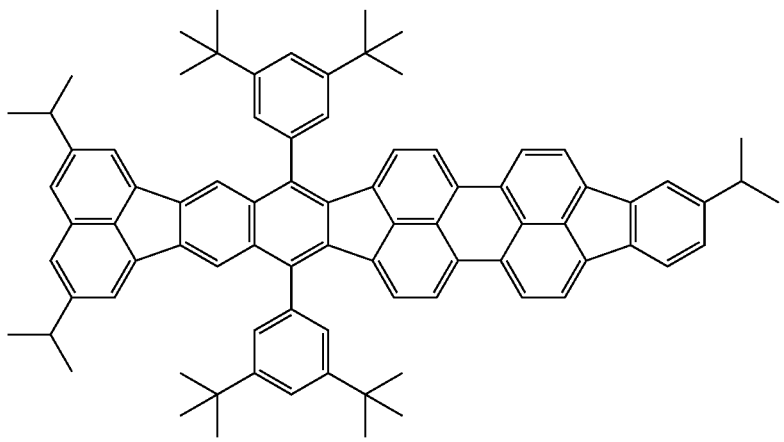
A13
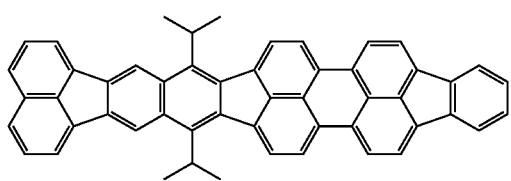
A14
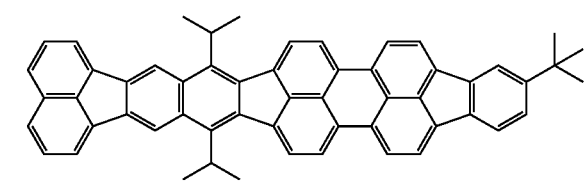
A15
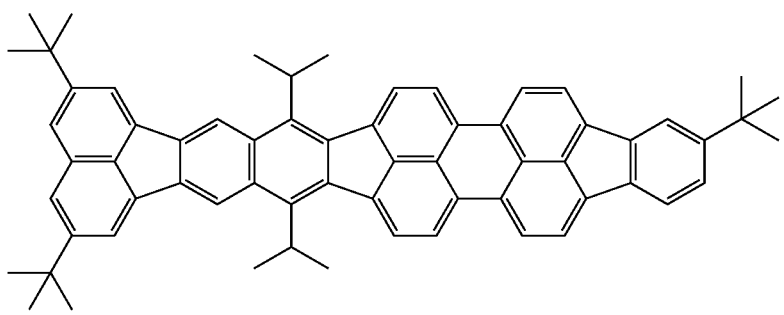
A16
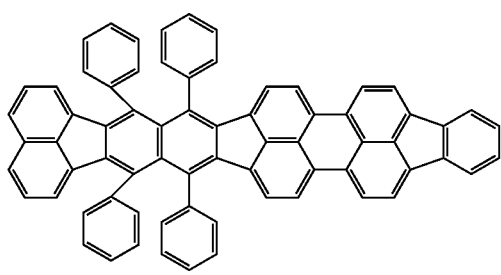
A17
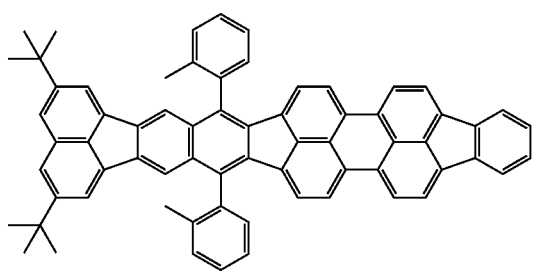
A18
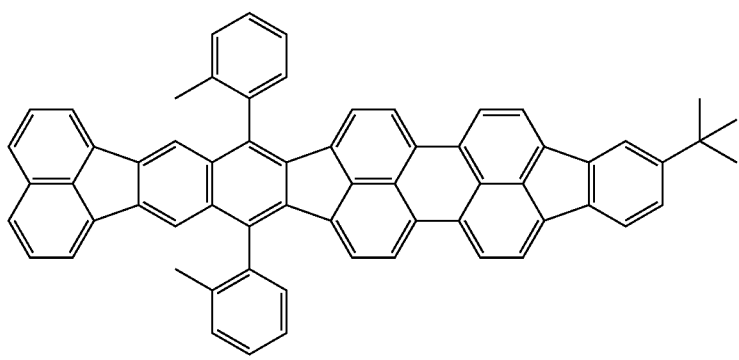

[Chem. 10]
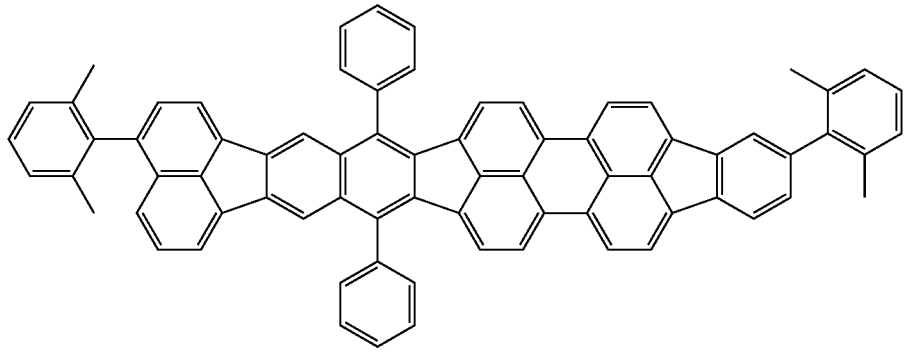
A19
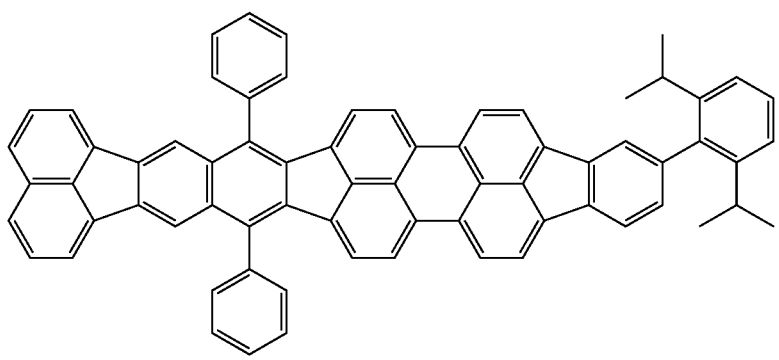
A20
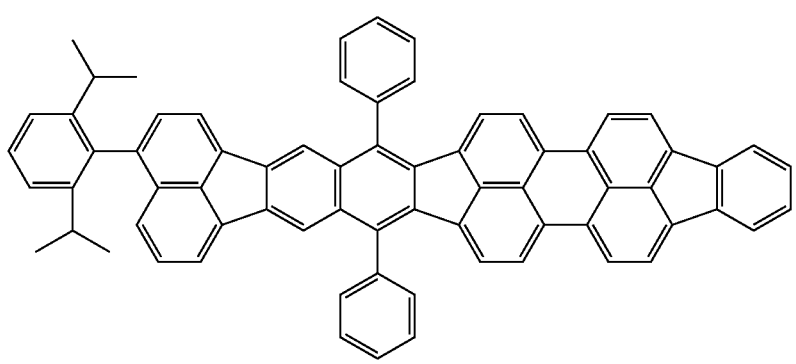
A21
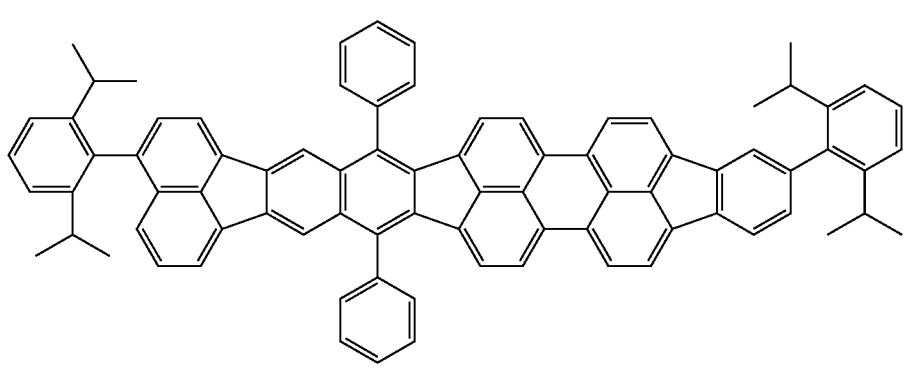
A22

-continued
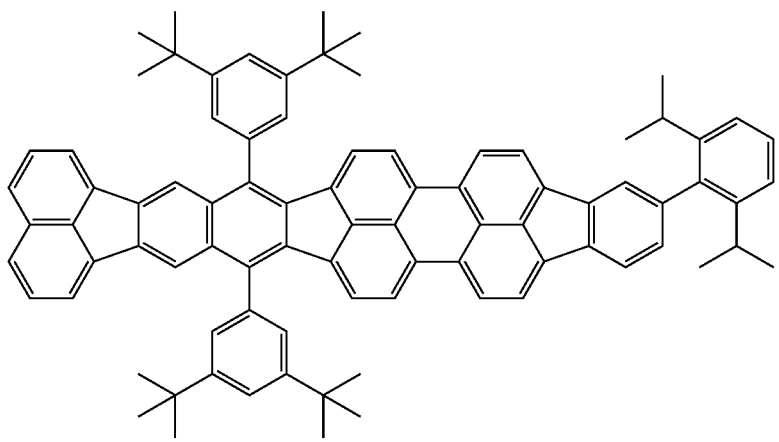
A23
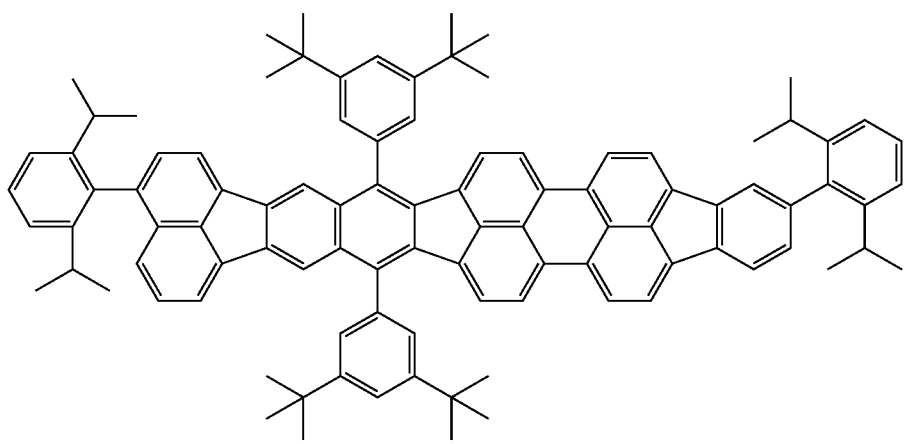
A24
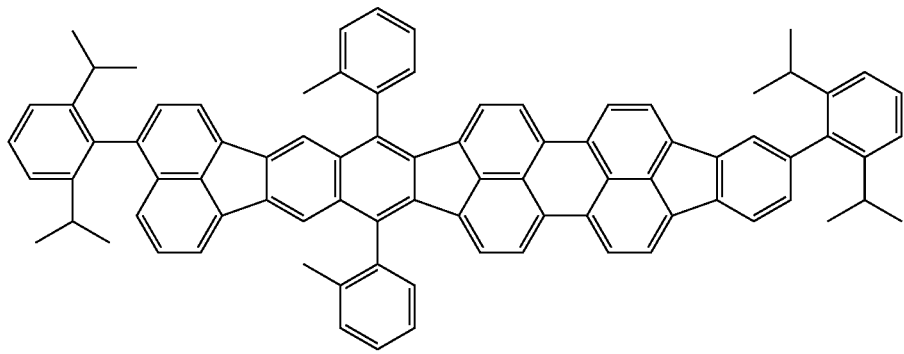
A25
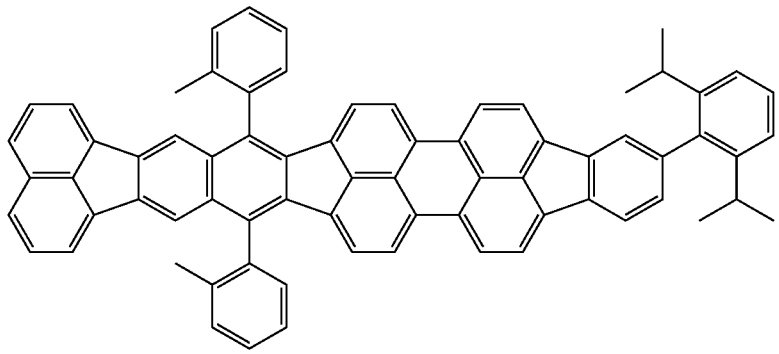
A26

-continued
A27
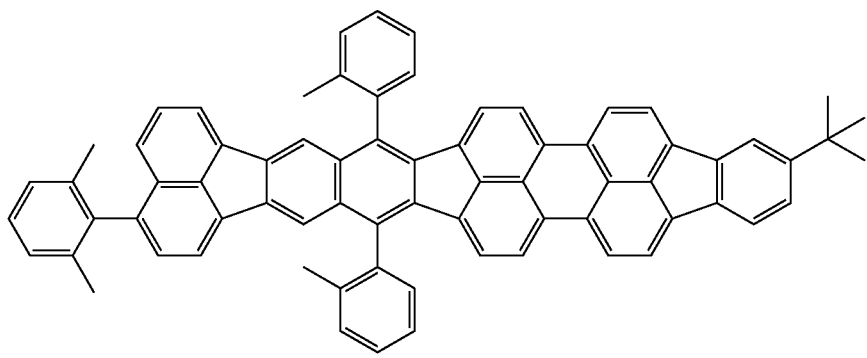
A28
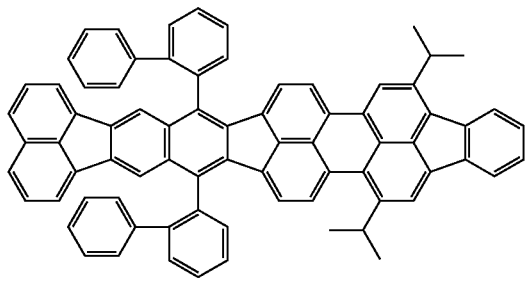
A29
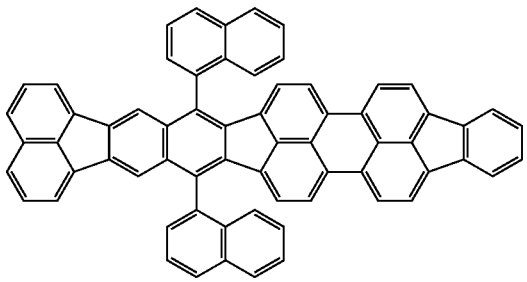
A30
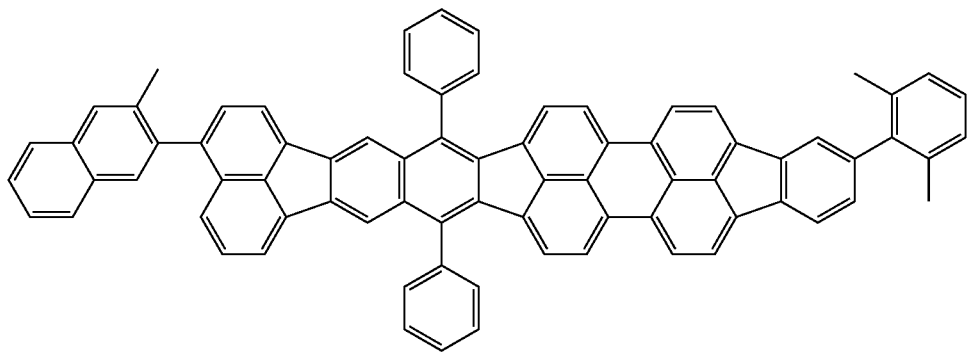
A31
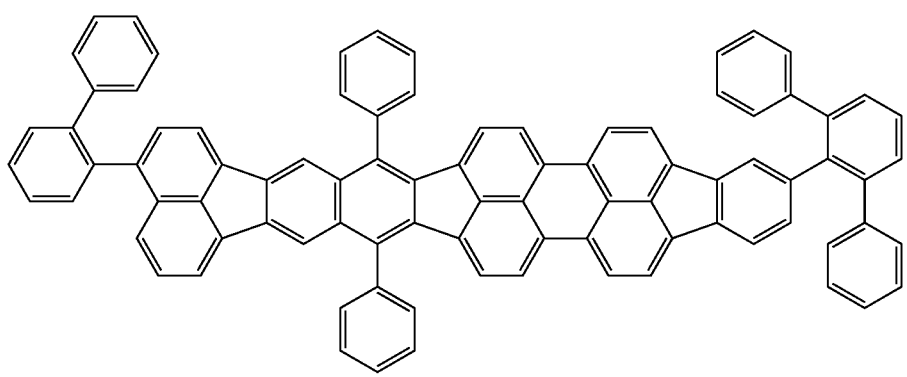

-continued
A32
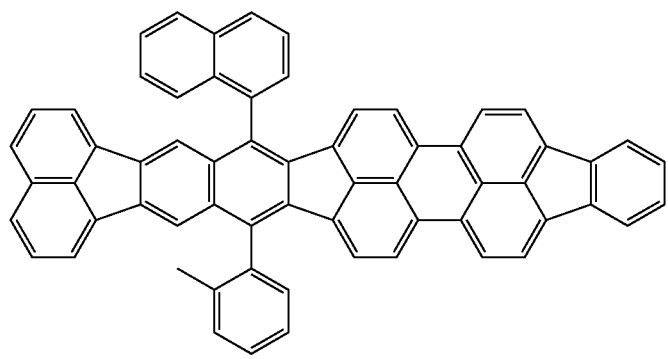
A33
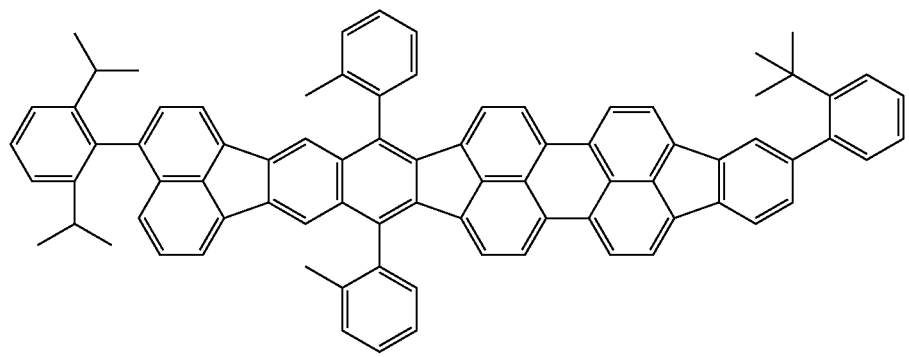
A34
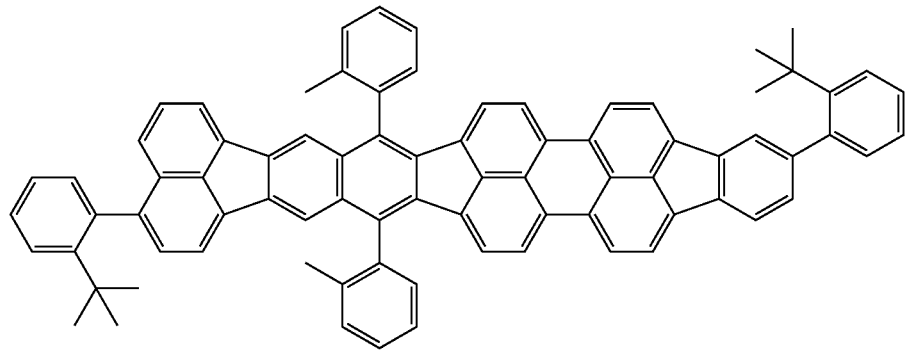
A35
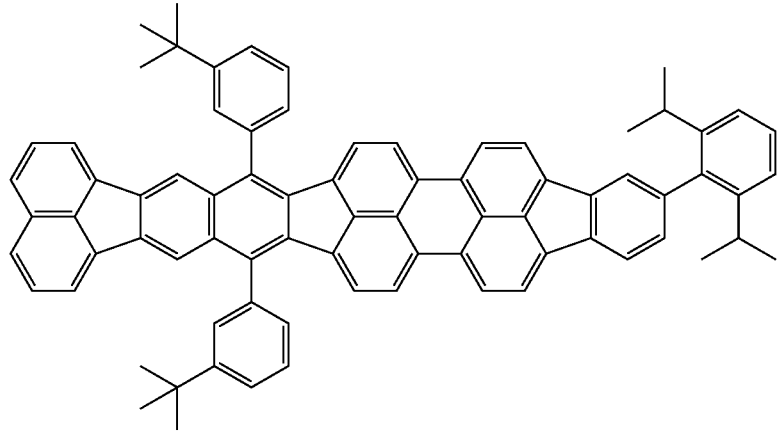

A36
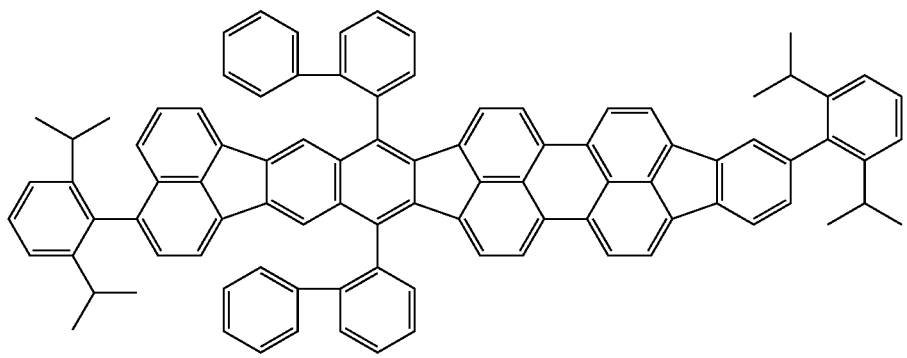
A37
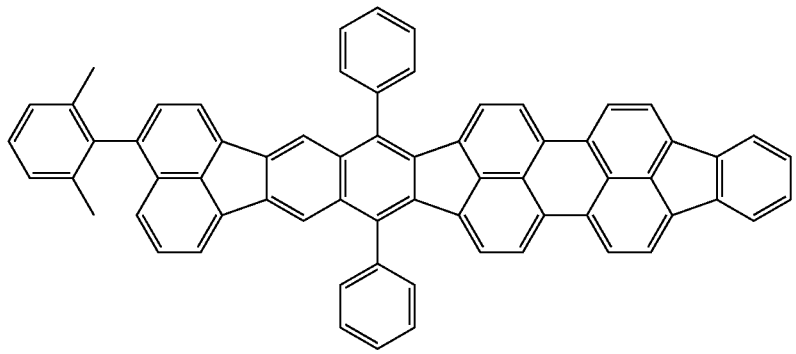
A38
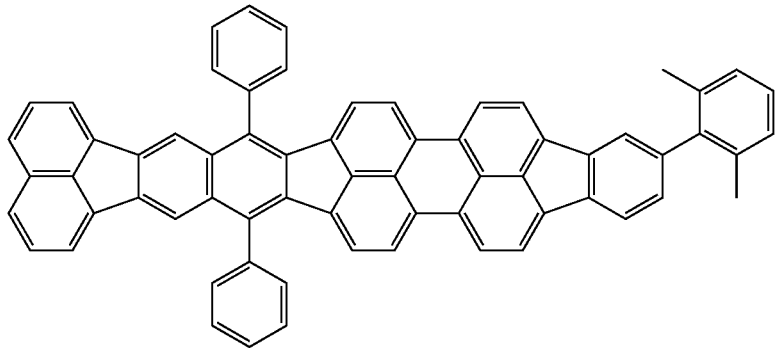
A39
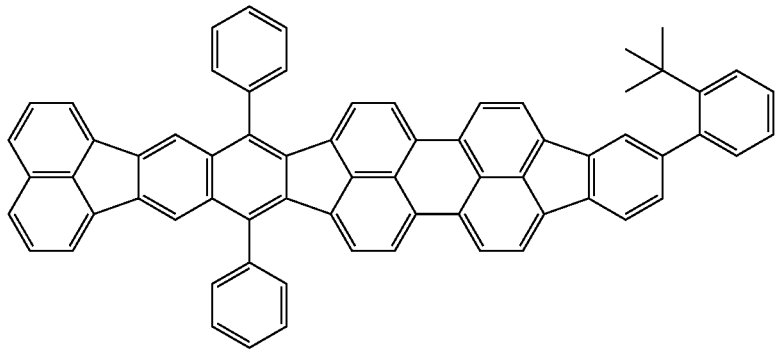

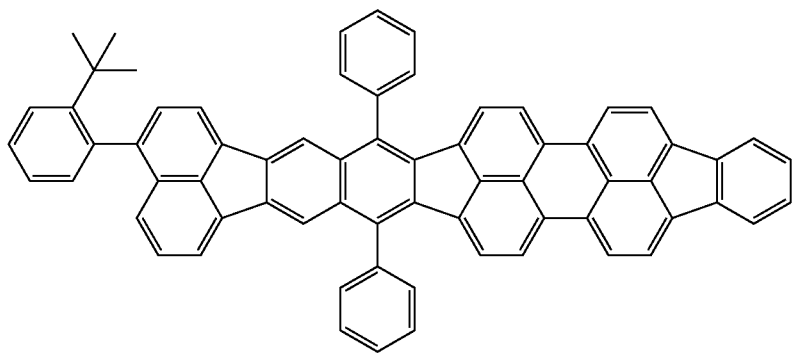
A40
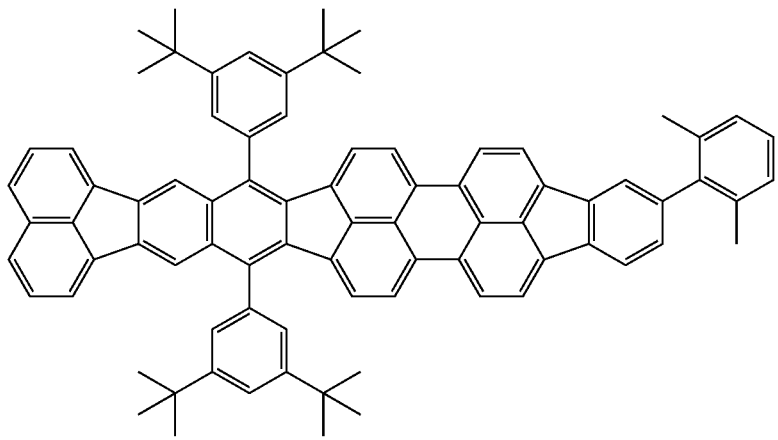
A41
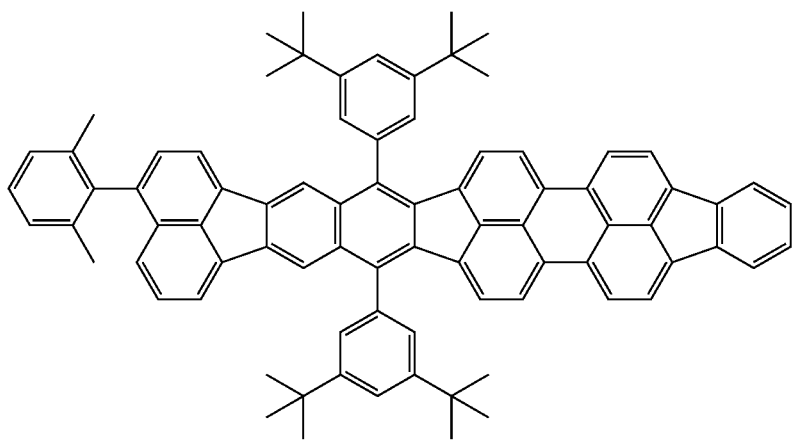
A42
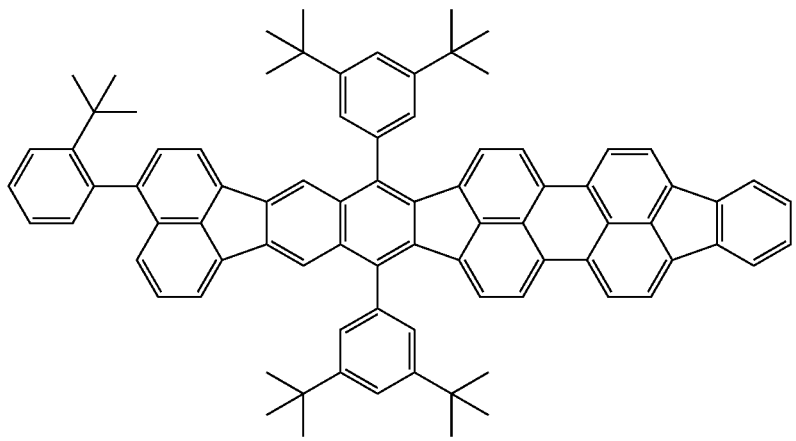
A43

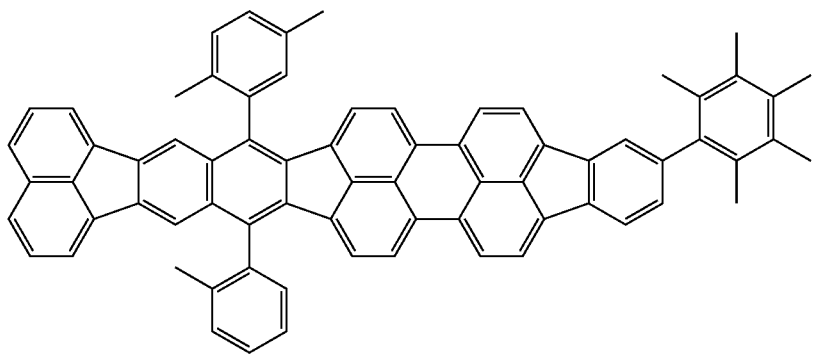
A44
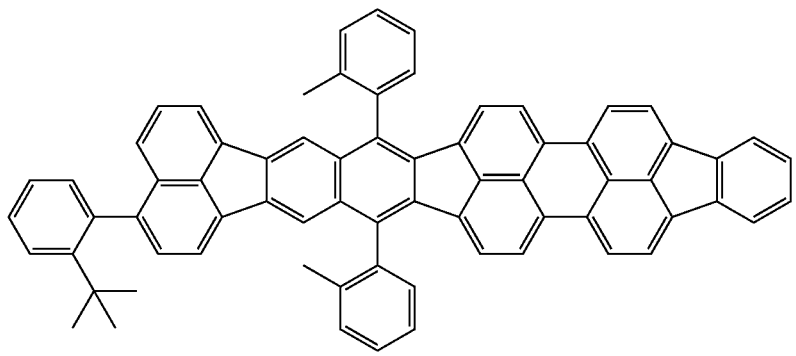
A45
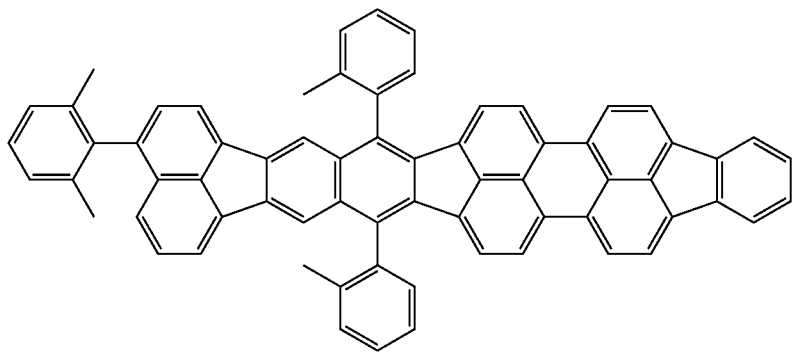
A46
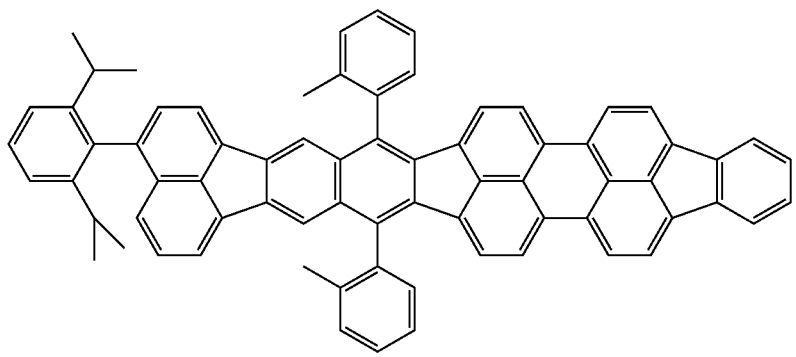
A47

-continued
A48
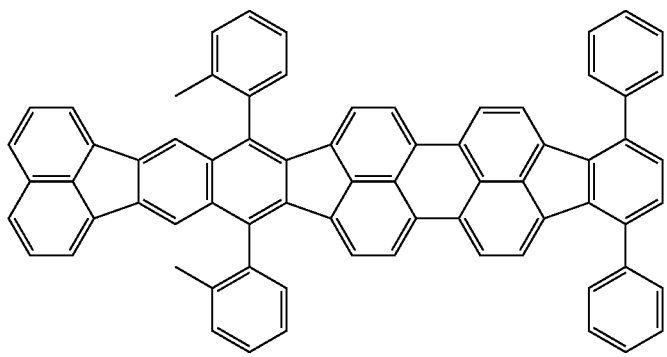
A49
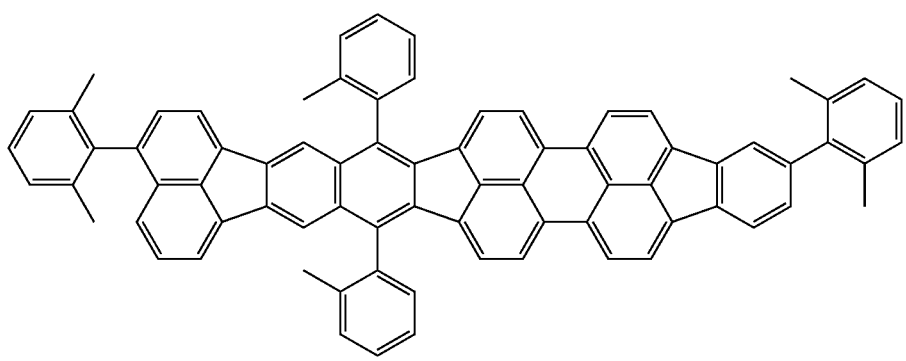
A50 A51
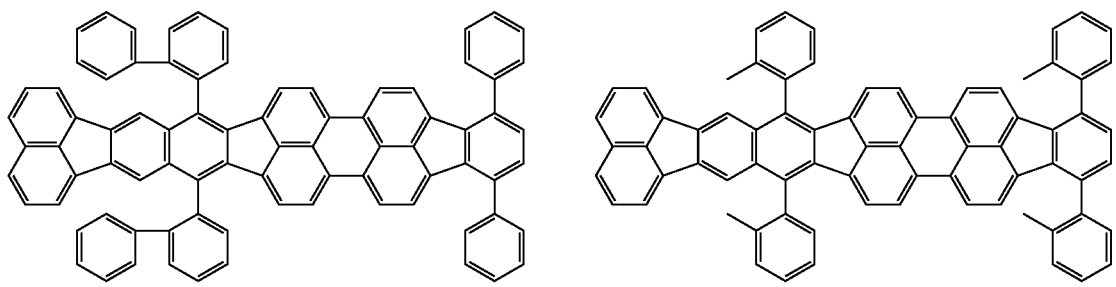
A52
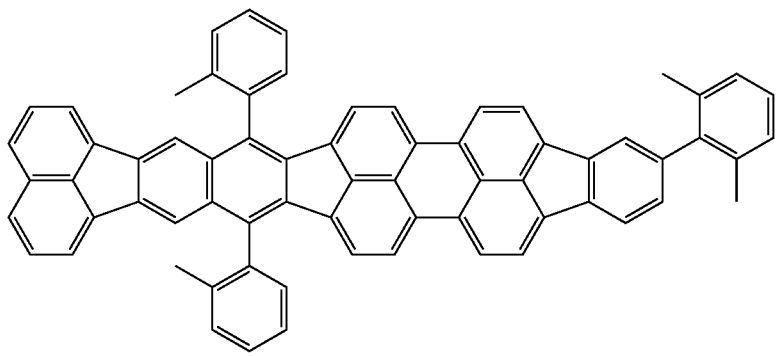

A53
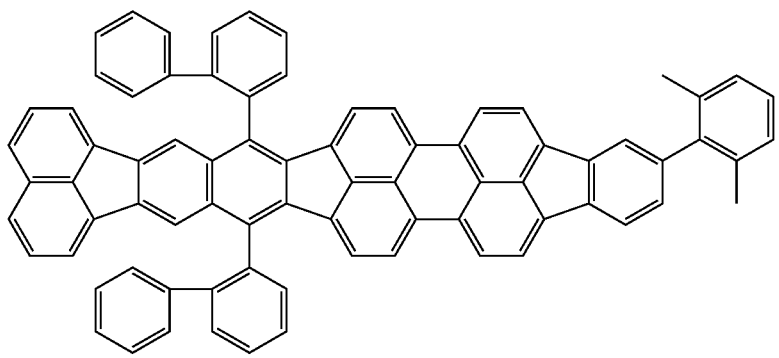
A54
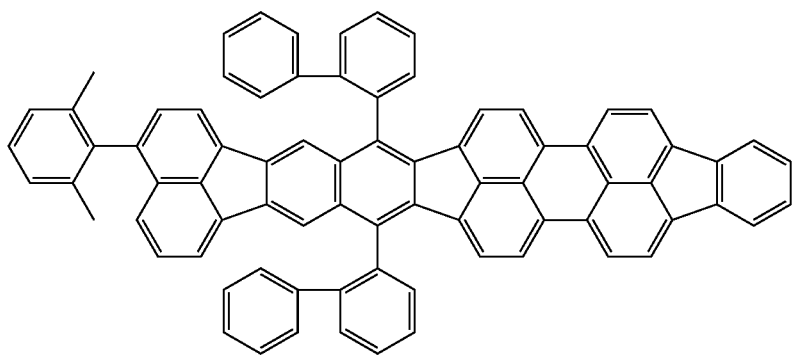
[Chem. 11]
B1
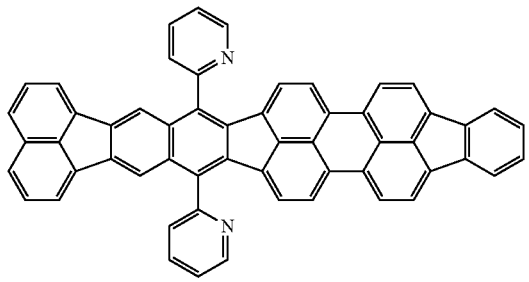
B2
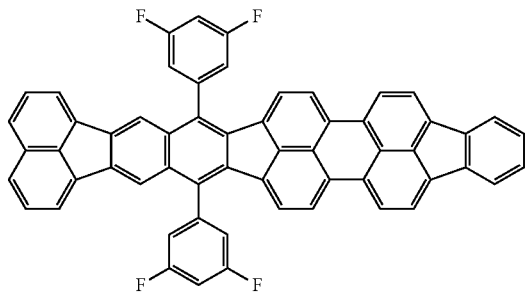
B3
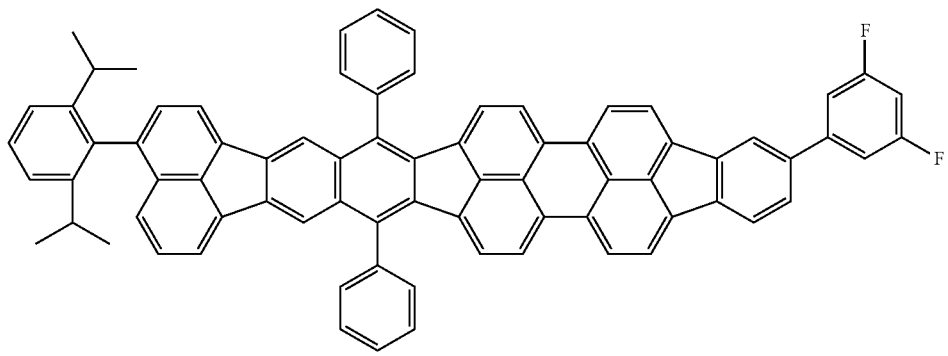

-continued
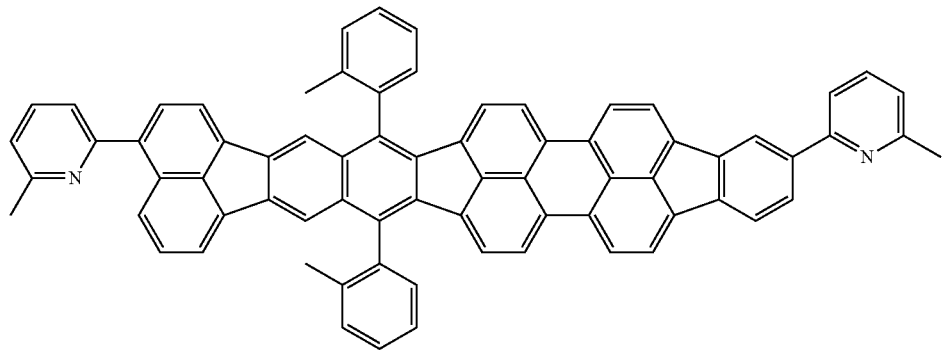
B4
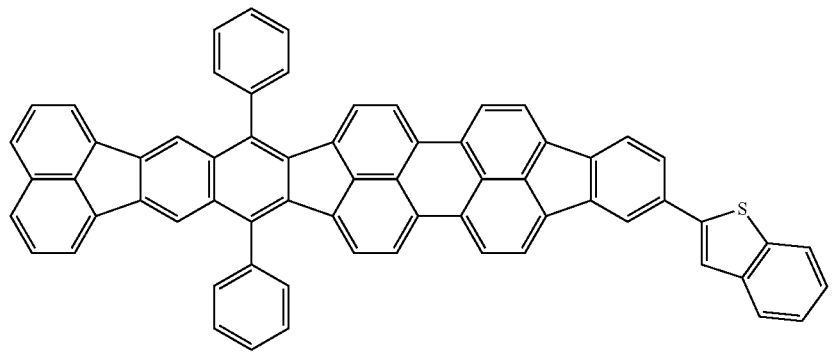
B5
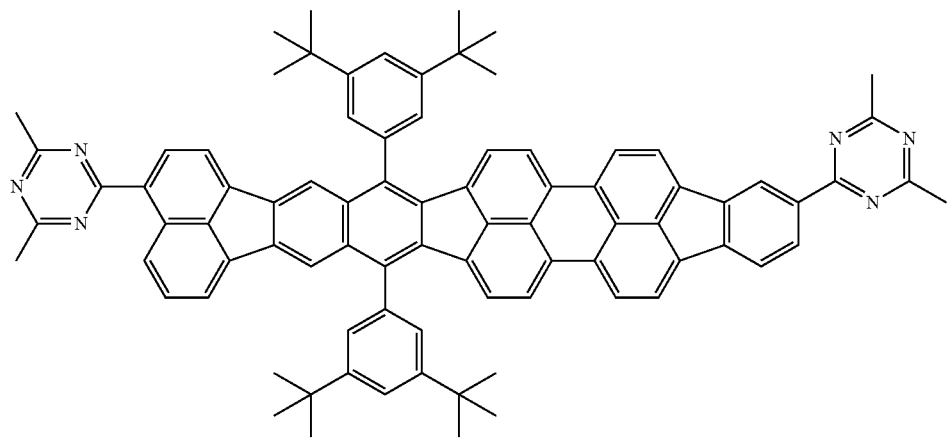
B6
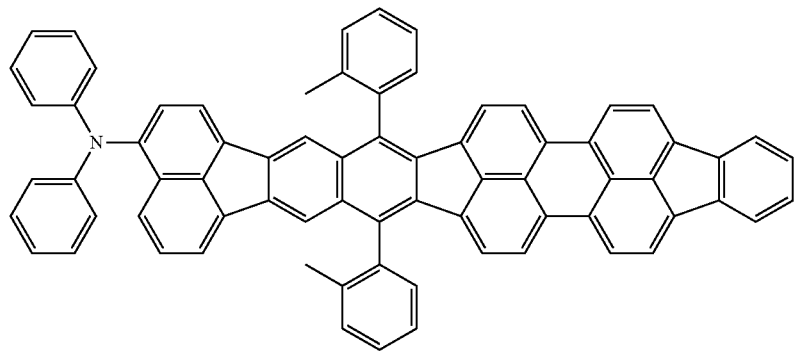
B7

-continued
B8
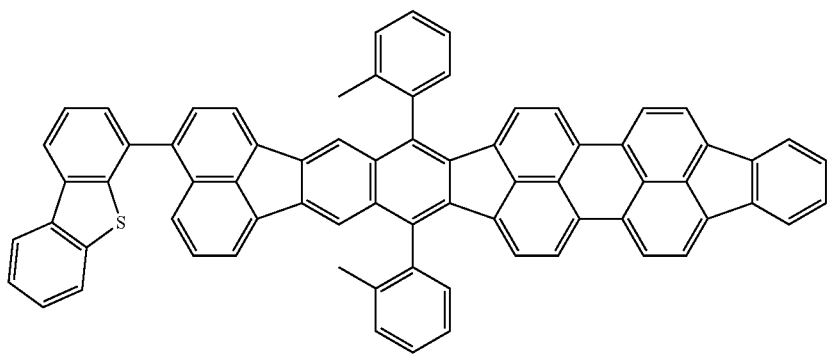
B9
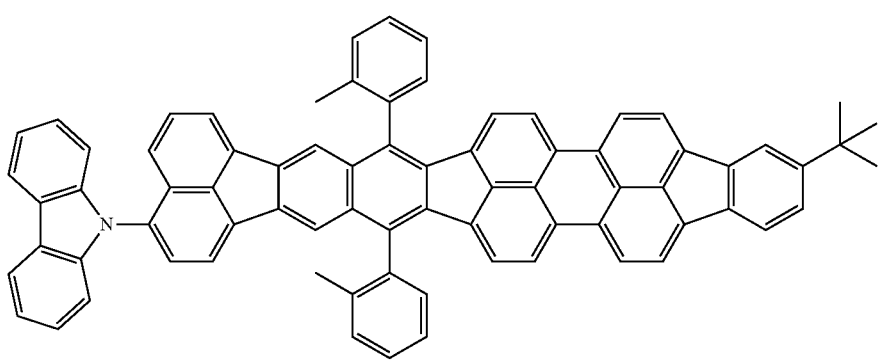
B10
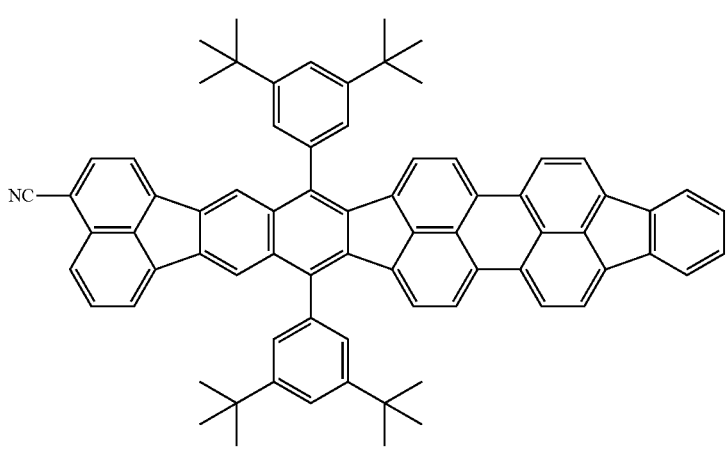
B11
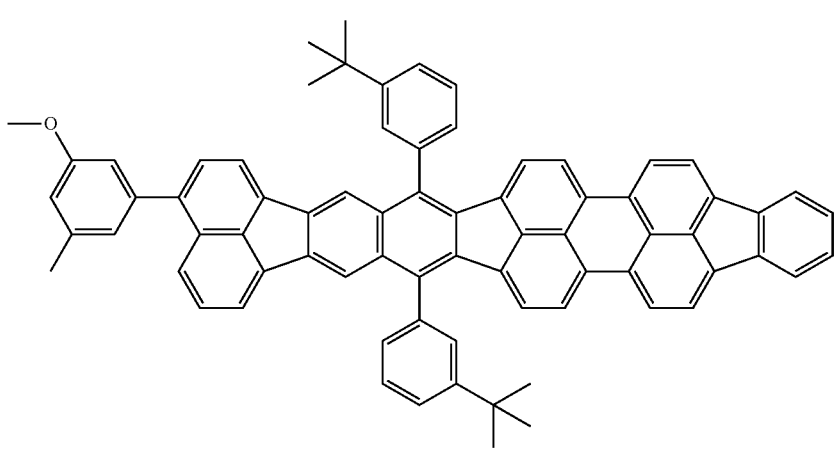

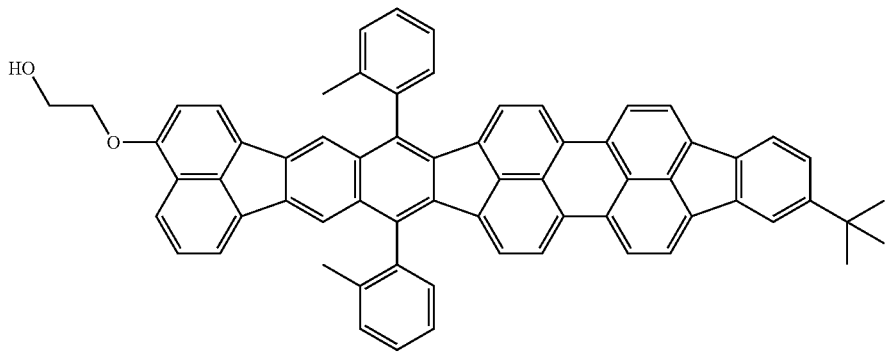

B12

In the compounds belonging to Group A among the exemplary compounds shown above, the entire molecules are constituted by only hydrocarbon. Herein, the compounds constituted by only hydrocarbon generally have a low LUMO energy level. Therefore, it means that the oxidation potential of the compounds belonging to Group A is low, i.e., the compounds are organic compounds stable to oxidization.

Therefore, the stability of the molecules of the organic compounds constituted by only hydrocarbon among the organic compounds according to this embodiment, i.e., the compounds belonging to Group A, is high, and thus are suitable. The organic compounds belonging to Group A can also be directly used for a light emitting layer, a transporting layer, and an injecting layer as a high-concentration material with a purity of up to 100%. When the organic compounds are used for a light emitting layer, the luminous efficiency decreases as compared with the case where the compounds are used at a low concentration. Here, the high concentration refers to a case where the organic compounds belonging to Group A are used with a purity of 50% or more and the low concentration refers to a case where the compounds are used with a purity of 10% or lower.

The position of the substituent is not particularly limited. It is suitable to introduce the substituent to a position at which the excimer generation is effectively suppressed. Specifically, the substituent is suitably located at the positions of $R_1$, $R_4$, $R_9$, $R_{10}$, $R_{17}$, and $R_{18}$ at which the substituent is likely to be orthogonal to the basic skeleton. Moreover, the substituent is suitably located at the positions of $R_2$, $R_3$, $R_{12}$, $R_{13}$, $R_{14}$, and $R_{15}$ which are effective for extending the distance between molecules.

In the compounds belonging to Group B among the exemplary compounds shown above, the substituent contains a hetero atom. In this case, the oxidation potential of the molecule itself greatly changes. Or, the intermolecular interaction changes. The organic compounds of Group B in which the substituent contains a hetero atom are useful as an electron transporting material, a hole transporting material, or a hole trap type light emitting material. Particularly in fluorine-substituted compounds, the intermolecular interaction is suppressed, and therefore an improvement of sublimation properties can be expected. The organic compounds belonging to Group B can also be directly used as a high-concentration material with a purity of up to 100%. Herein, the high concentration refers to a case where the organic compounds belonging to Group B are used with a purity of 50% or more and the low concentration refers to a case where the compounds are used with a purity of 10% or lower.

Next, an organic light emitting device of this embodiment is described.

The organic light emitting device of this embodiment at least has an anode and a cathode which form a pair of electrodes and an organic compound layer disposed between these electrodes. In the organic light emitting device of this embodiment, the organic compound layer may be a single layer or a laminate containing a plurality of layers insofar as the organic light emitting device has a light emitting layer.

Herein, when the organic compound layer is a laminate containing a plurality of layers, the organic compound layer may have a hole injecting layer, a hole transporting layer, an electron blocking layer, a hole/exciton blocking layer, an electron transporting layer, an electron injecting layer, and the like in addition to the light emitting layer. The light emitting layer may be a single layer or a laminate containing a plurality of layers.

In the organic light emitting device of this embodiment, the organic compound according to this embodiment is contained in at least one layer of the organic compound layers described above. Specifically, the organic compound according to this embodiment is contained in any one of the light emitting layer, the hole injecting layer, the hole transporting layer, the electron blocking layer, the light emitting layer, the hole/exciton blocking layer, the electron transporting layer, the injecting layer, and the like mentioned above. The organic compound according to this embodiment is suitably contained in the light emitting layer.

In the organic light emitting device of this embodiment, when the organic compound according to this embodiment is contained in the light emitting layer, the light emitting layer may be a layer containing only the organic compound according to this embodiment or may be a layer containing the organic compound according to this embodiment and other compounds. Herein, when the light emitting layer is a layer containing the organic compound according to this embodiment and other compounds, the organic compound according to this embodiment may be used as a host of the light emitting layer or may be used as a guest. Or, the organic compound according to this embodiment may be used as an assistant material which can be contained in the light emitting layer.

Herein, the host is a compound with the highest weight ratio among the compounds constituting the light emitting layer. The guest is a compound whose weight ratio is lower than that of the host among the compounds constituting the light emitting layer and is a compound which performs main light emission. The assist material is a compound whose weight ratio is lower than that of the host among the compounds constituting the light emitting layer and is a compound which assists the light emission of the guest. The assist material is also referred to as a second host.

Herein, when the organic compound according to this embodiment is used as the guest of the light emitting layer, the concentration of the guest is suitably 0.01% by weight or more and 20% by weight or lower and more suitably 0.1% by weight or more and 5% by weight or lower based on the entire light emitting layer.

When the organic compound according to this embodiment is used as the guest of the light emitting layer, it is suitable to use a material having LUMO higher than that of the organic compound according to this embodiment (material in which LUMO is closer to the vacuum level) as the host. This is because the LUMO of the organic compound according to this embodiment is low, and therefore, by using a material whose LUMO is higher than that of the organic compound according to this embodiment as the host, the organic compound according to this embodiment can receive a larger number of electrons to be supplied to the host of the light emitting layer.

The present inventors have conducted various examinations, and have found that when the organic compound according to this embodiment is used as the host or the guest of the light emitting layer, particularly as the guest of the light emitting layer, a device is obtained which outputs light with high efficiency and high luminance and has extremely high durability. The light emitting layer may be a single layer or a multilayer. By compounding a light emitting material which emits light of another color, the light color thereof can be mixed with red light color which is the light color of this embodiment. The multilayer means a state where the light emitting layer and another light emitting layer are laminated. In this case, the light color of the organic light emitting device is not limited to red. More specifically, white color may be acceptable or an intermediate color may be acceptable. In the case of white color, the other light emitting layer emits light of color other than red, i.e., blue light or green light. Film formation is performed by a film formation method, such as vapor deposition or a coating film formation. The details are described in detail in Examples described later.

The organic compound according to this embodiment can be used as a constituent material of the organic compound layer other than the light emitting layer constituting the organic light emitting device of this embodiment. Specifically, the organic compound according to this embodiment may be used as a constituent material of the electron transporting layer, the electron injecting layer, the hole transporting layer, the hole injecting layer, the hole blocking layer, or the like. In this case, the light color of the organic light emitting device is not limited to red. More specifically, white color may be acceptable or an intermediate color may be acceptable.

Herein, besides the organic compound according to this embodiment, various kinds of low molecular weight type and high molecular weight type hole injectable compounds or hole transportable compounds, compounds serving as a host, light emitting compounds, electron injectable compounds or electron transportable compounds, and the like can be used together as required.

Examples of the compounds are shown below.

The hole injectable compounds and the hole transportable compounds are suitably materials having a high hole movement degree. Mentioned as the low molecular weight compounds or high molecular weight compounds having hole injection capability or hole transportation capability are a triarylamine derivative, a phenylenediamine derivative, a stilbene derivative, a phthalocyanine derivative, a porphyrin derivative, poly(vinylcarbazole), poly(thiophene), and other conductive polymers but the compounds are not limited thereto.

As the host, the compounds shown in the following Table 2 are specifically mentioned.

TABLE 2

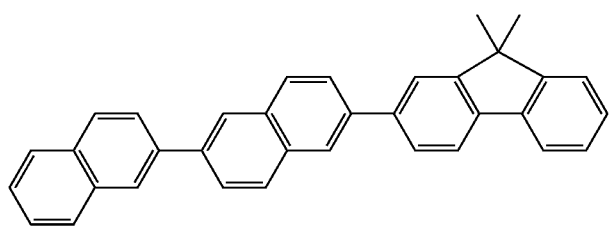 [SMILES: CC1(C)c2ccccc2-c2ccc(-c3ccc4cc(-c5ccc6ccccc6c5)ccc4c3)cc21]

H1

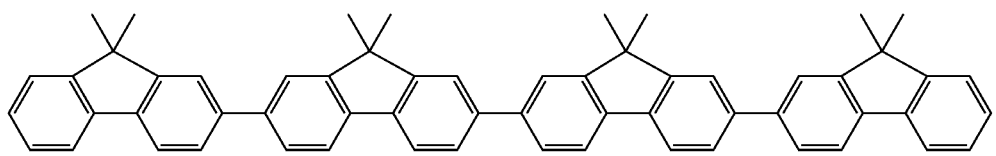 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

H2

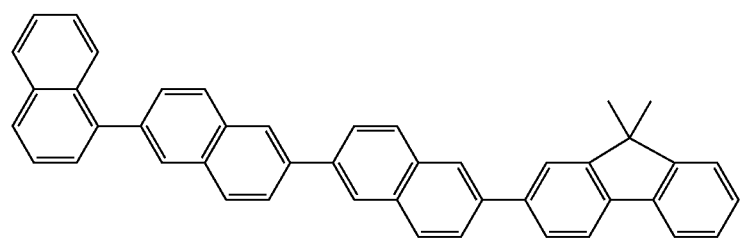 [SMILES: CC1(C)c2ccccc2-c2ccc(-c3ccc4cc(-c5ccc6cc(-c7cccc8ccccc78)ccc6c5)ccc4c3)cc21]

H3

TABLE 2-continued
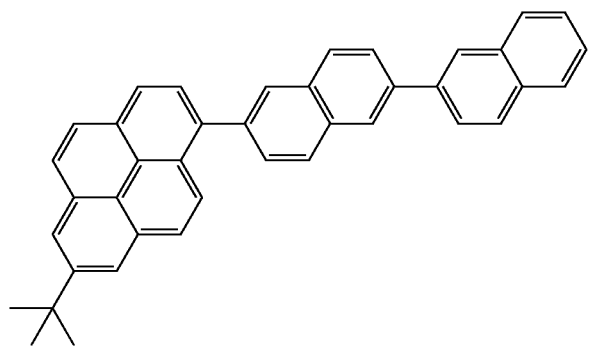 [SMILES: CC(C)(C)c1cc2ccc3ccc(-c4ccc5cc(-c6ccc7ccccc7c6)ccc5c4)c4ccc(c1)c2c34] H4
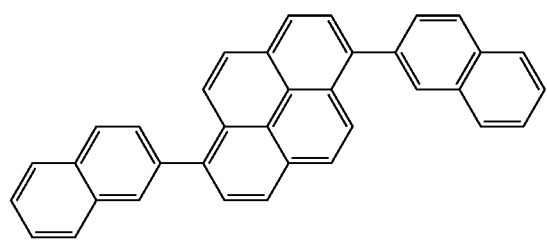 [SMILES: c1ccc2cc(-c3ccc4ccc5c(-c6ccc7ccccc7c6)ccc6ccc3c4c65)ccc2c1] H5
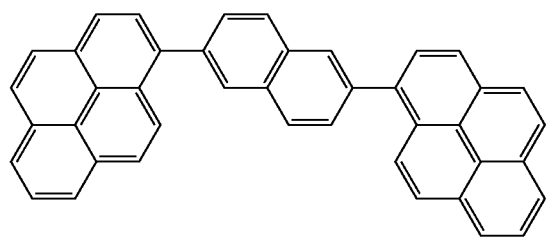 [SMILES: c1cc2ccc3ccc(-c4ccc5cc(-c6ccc7ccc8cccc9ccc6c7c89)ccc5c4)c4ccc(c1)c2c34] H6
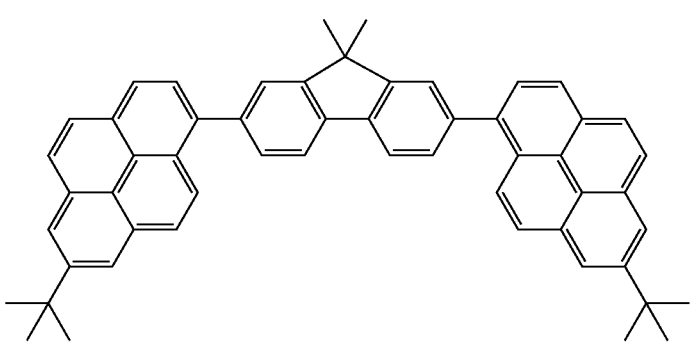 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H7
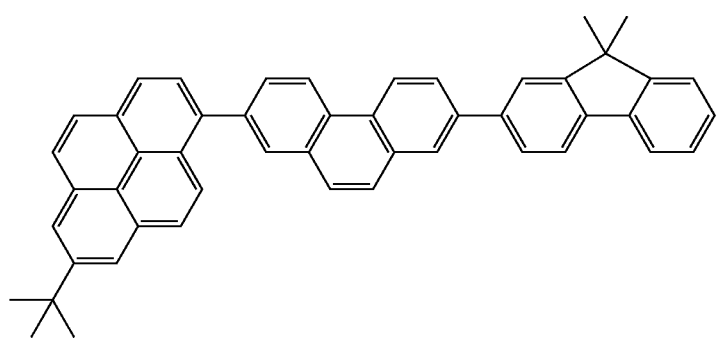 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] H8

TABLE 2-continued
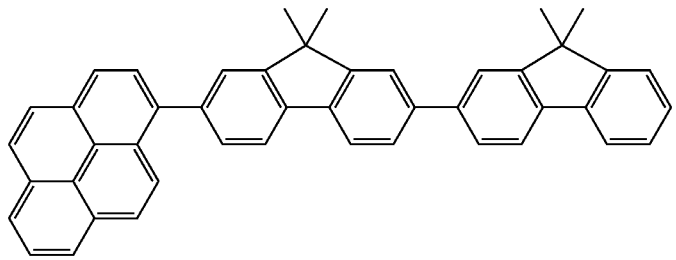 [SMILES: CC1(C)c2ccccc2-c2ccc(-c3ccc4c(c3)C(C)(C)c3cc(-c5ccc6ccc7cccc8ccc5c6c78)ccc3-4)cc21] H9
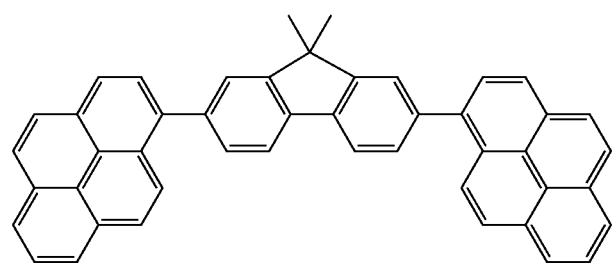 [SMILES: CC1(C)c2cc(-c3ccc4ccc5cccc6ccc3c4c56)ccc2-c2ccc(-c3ccc4ccc5cccc6ccc3c4c56)cc21] H10
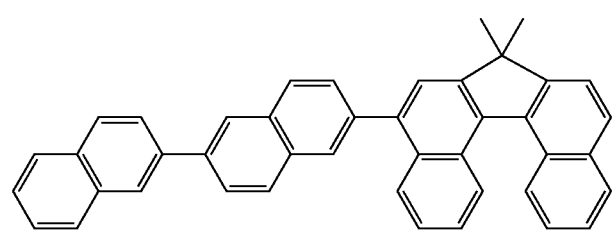 [SMILES: CC1(C)c2ccc3ccccc3c2-c2c1cc(-c1ccc3cc(-c4ccc5ccccc5c4)ccc3c1)c1ccccc21] H11
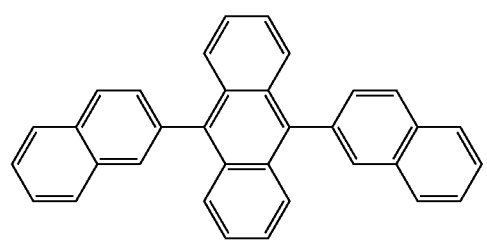 [SMILES: c1ccc2cc(-c3c4ccccc4c(-c4ccc5ccccc5c4)c4ccccc34)ccc2c1] H12
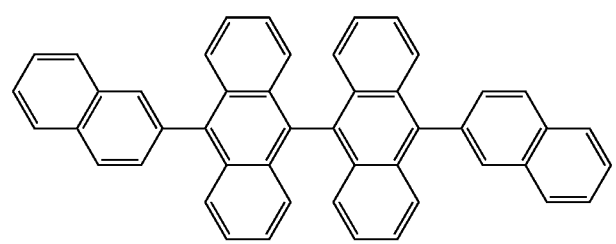 [SMILES: c1ccc2cc(-c3c4ccccc4c(-c4c5ccccc5c(-c5ccc6ccccc6c5)c5ccccc45)c4ccccc34)ccc2c1] H13
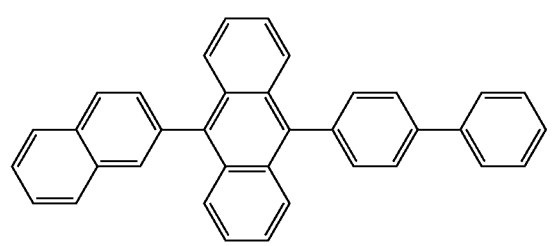 [SMILES: c1ccc(-c2ccc(-c3c4ccccc4c(-c4ccc5ccccc5c4)c4ccccc34)cc2)cc1] H14

TABLE 2-continued
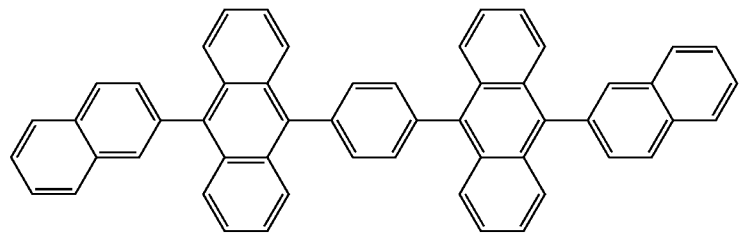 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H15
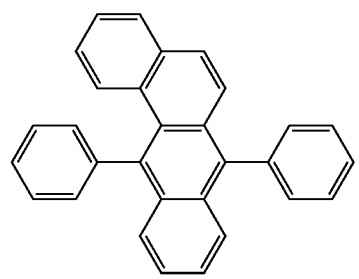 [SMILES: c1ccc(-c2c3ccccc3c(-c3ccccc3)c3c2ccc2ccccc23)cc1] H16
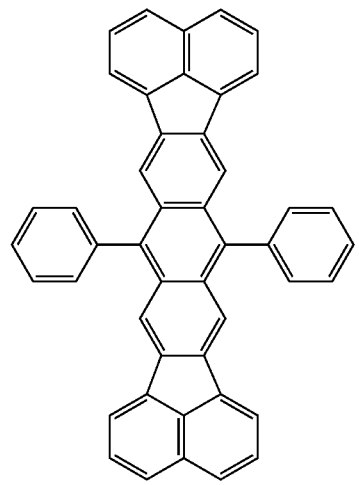 [SMILES: c1ccc(-c2c3cc4c(cc3c(-c3ccccc3)c3cc5c(cc23)-c2cccc3cccc-5c23)-c2cccc3cccc-4c23)cc1] H17
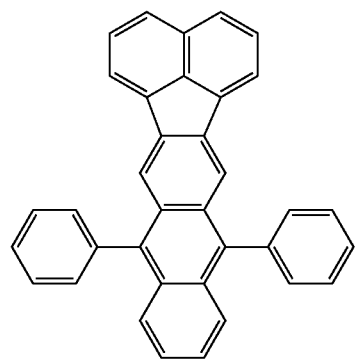 [SMILES: c1ccc(-c2c3ccccc3c(-c3ccccc3)c3cc4c(cc23)-c2cccc3cccc-4c23)cc1] H18

TABLE 2-continued
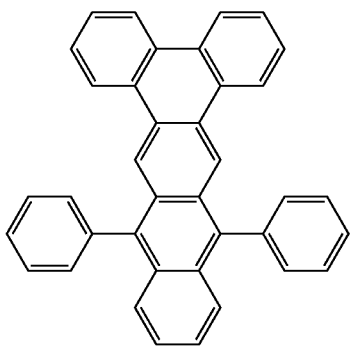 [SMILES: c1ccc(-c2c3ccccc3c(-c3ccccc3)c3cc4c5ccccc5c5ccccc5c4cc23)cc1]
H19
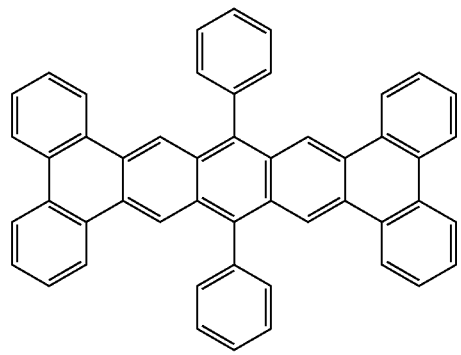 [SMILES: c1ccc(-c2c3cc4c5ccccc5c5ccccc5c4cc3c(-c3ccccc3)c3cc4c5ccccc5c5ccccc5c4cc23)cc1]
H20
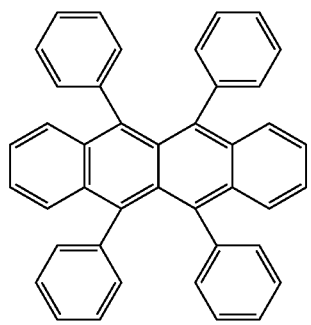 [SMILES: c1ccc(-c2c3ccccc3c(-c3ccccc3)c3c(-c4ccccc4)c4ccccc4c(-c4ccccc4)c23)cc1]
H21
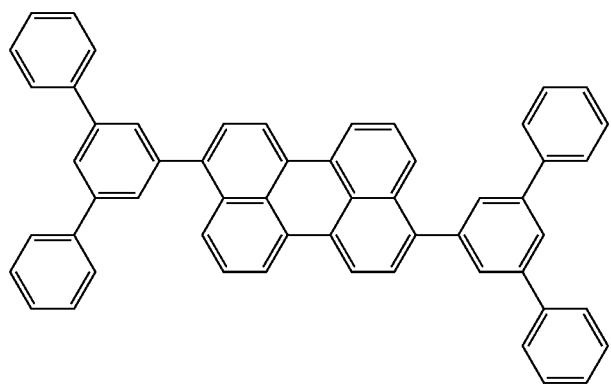 [SMILES: c1ccc(-c2cc(-c3ccccc3)cc(-c3ccc4c5cccc6c(-c7cc(-c8ccccc8)cc(-c8ccccc8)c7)ccc(c7cccc3c74)c65)c2)cc1]
H22

TABLE 2-continued

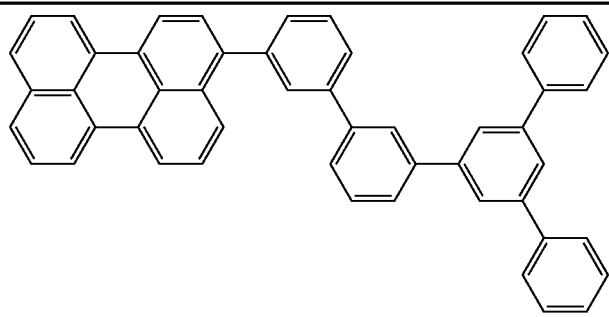
H23

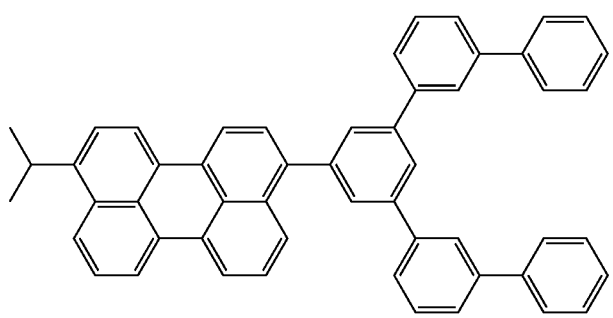 [SMILES: CC(C)c1ccc2c3ccc(-c4cc(-c5cccc(-c6ccccc6)c5)cc(-c5cccc(-c6ccccc6)c5)c4)c4cccc(c5cccc1c52)c43]
H24

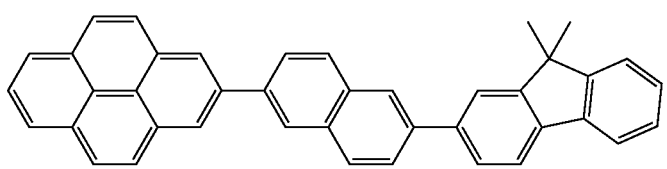 [SMILES: CC1(C)c2ccccc2-c2ccc(-c3ccc4cc(-c5cc6ccc7cccc8ccc(c5)c6c78)ccc4c3)cc21]
H25

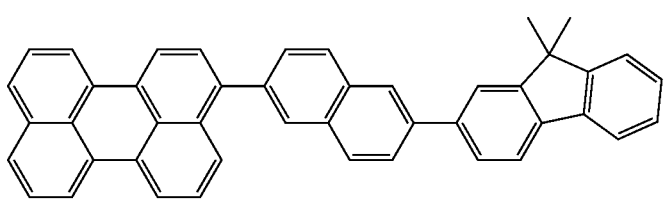 [SMILES: CC1(C)c2ccccc2-c2ccc(-c3ccc4cc(-c5ccc6c7cccc8cccc(c9cccc5c96)c87)ccc4c3)cc21]
H26

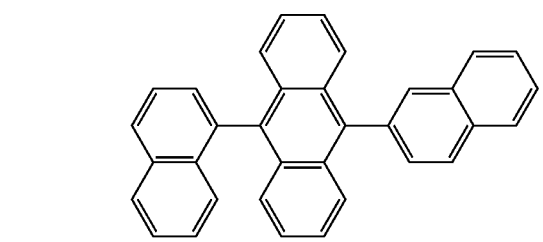 [SMILES: c1ccc2cc(-c3c4ccccc4c(-c4cccc5ccccc45)c4ccccc34)ccc2c1]
H27

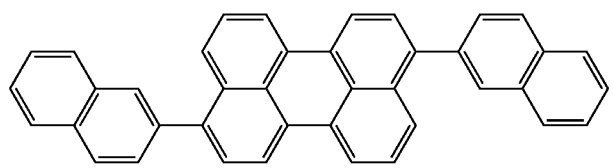 [SMILES: c1ccc2cc(-c3ccc4c5cccc6c(-c7ccc8ccccc8c7)ccc(c7cccc3c74)c65)ccc2c1]
H28

However, the invention is not limited thereto. Compounds which are derivatives of the compounds shown in Table 2 can also be used as the host. In addition to the compounds, a condensed compound (e.g., a fluorene derivative, a naphthalene derivative, an anthracene derivative, a pyrene derivative, a carbazole derivative, a quinoxaline derivative, and a quinoline derivative), an organic aluminum complex, such as tris(8-quinolinolato)aluminum, and a high molecular weight derivative, such as an organic zinc complex, a triphenylamine derivative, a poly(fluorene) derivative, and a poly(phenylene) derivative, are mentioned but the invention is not limited thereto.

As the electron injectable compound and the electron transportable compound, compounds are selected as appropriate considering, for example, the balance with the hole movement degree of the hole injectable compound and the hole transportable compound. Mentioned as the compound having electron injection capability or electron transportation capability are an oxadiazole derivative, an oxazole derivative, a pyrazine derivative, a triazole derivative, a triazine derivative, a quinoline derivative, a quinoxaline derivative, a phenanthroline derivative, an organic aluminium complex, and the like but the compound is not limited thereto.

As a constituent material of an anode, materials having as high a work function as possible are suitably used. For example, mentioned are simple metal substances, such as gold, platinum, silver, copper, nickel, palladium, cobalt, selenium, vanadium, and tungsten, or an alloy obtained by combining a plurality of the simple metal substances, and metal oxides, such as tin oxide, zinc oxide, indium oxide, indium tin oxide (ITO), and indium zinc oxide. Conductive polymers, such as polyaniline, polypyrrole, and polythiophene, may be acceptable. These electrode substances may be used singly or a plurality kinds of the substances may be used in combination. The anode may be a single layer structure or a multilayer structure.

As a constituent material of a cathode, materials having a low work function are suitably used. For example, mentioned are alkaline metals, such as lithium, alkaline earth metals, such as calcium, simple metal substances, such as aluminum, titanium, manganese, silver, lead, and chromium. Or, alloy obtained by combining a plurality of the simple metal substances can also be used. For example, magnesium-silver, aluminum-lithium, aluminum-magnesium, and the like can be used. Metal oxides, such as indium tin oxide (ITO), can also be utilized. These electrode substances may be used singly or a plurality kinds of the substances may be used in combination. The cathode may be a single layer structure or a multilayer structure.

In the organic light emitting device of this embodiment, the layer containing the organic compound according to this embodiment and the layer containing the other organic compound are formed by the following methods. In general, a thin film is formed by a vacuum deposition method, an ionization vapor deposition method, sputtering, plasma, or a known coating method (e.g., spin coating, dipping, a casting method, an LB method, and an inkjet method) after dissolving the organic compound in a suitable solvent. When a layer is formed by a vacuum deposition method, a solution coating method, or the like herein, crystallization is difficult to occur and the stability with time is excellent. When forming a film by a coating method, a film can also be formed in combination with a suitable binder resin.

Mentioned as the binder resin are polyvinyl carbazole resin, polycarbonate resin, polyester resin, ABS resin, acrylic resin, polyimide resin, phenol resin, epoxy resin, silicone resin, urea resin, and the like but the binder resin is not limited thereto. The binder resins may be used singly as a homopolymer or a copolymer or as a mixture of two or more kinds thereof. Furthermore, additives, such as a known plasticizer, an antioxidant agent, and a UV absorber, may be used in combination as required.

The organic light emitting device of the invention can be used as a constituent member of a display device or a lighting device. In addition thereto, the organic light emitting device of the invention is applied to an exposure light source of an electrophotographic image formation device, a back light of a liquid crystal display, a color-filter-less white light source, a light emitting device having a color filter and a white light source, and the like. The color filter is a filter through which at least one of three colors of red, green, and blue colors passes, for example. The light emitting device may have a filter for adjusting the chromaticity of white color and a white light source in combination.

The display device has the organic light emitting device of this embodiment at a display portion. The display portion has a plurality of pixels. The pixel has the organic light emitting device of this embodiment and a transistor which is an example of a switching element or an amplifier element for controlling the light emission luminosity, and the anode or the cathode of the organic light emitting device and the drain electrode or the source electrode of the transistor are electrically connected. Herein, the display device can be used as an image display device of PC and the like.

The display device may be an image input device which has an input portion which inputs image information from an area CCD, a linear CCD, a memory card, or the like and which outputs the input image to a display portion. As a display portion of an image pickup device or an inkjet printer, both an image output function for displaying image information from the outside and an input function for inputting processing information to an image as an operation panel may be provided. The display device may also be used for the display portion of a multifunction printer.

The lighting device is a device which illuminates the inside of a room. The lighting device may be one which emits light of any one of white color, daylight white color, and other colors of blue to red. The lighting device may have the organic light emitting device according to this embodiment and an inverter circuit to be connected thereto. The white color refers to one having a color temperature of 4200 K and the daylight white color refers to one having a color temperature of 5000 K. The lighting device may have a color filter.

The compound of the invention can be used for a fluorescence recognition material, a film, a filter, and the like of an organic solar cell, an organic TFT, a living body, and the like in addition to the organic light emitting device.

When used as an exposure light source for an electrophotographic image formation device, a plurality of organic light emitting devices are disposed in one row. Thus, each of the organic light emitting devices correspond to each other, an exposure light source can be provided in which a plurality of light emitting points are disposed in the shape of a line. Then, an electrophotographic image formation device, such as a laser beam printer or a copying machine, having the exposure light source and a photoconductor drum exposed by light emitted from the exposure light source can be provided.

An image pickup device has an optical system in an image pick-up portion. The image pickup device is a device which electronizes a photographed image to obtain image information. For example, a digital camera, a digital video camera, and a cellular phone can be mentioned. An image display device has a display portion at the back surface and may have a display portion as an interface portion which displays an image from the image information obtained by the image pickup device or prescribes image pick-up conditions and the like to the image pickup device.

The image pickup device may further have an image display device having the organic light emitting device at a finder portion.

Next, a display device employing the organic light emitting device of this embodiment is described with reference to FIG. 1.

FIG. 1 is a cross-sectional schematic view illustrating an example of a display device having the organic light emitting device of this embodiment and a TFT element which is an example of a transistor connected to the organic light emitting device. In a display device 20 of FIG. 1, two pairs of the organic light emitting device and the TFT element are illustrated. The details of the structure are described below.

The display device 20 of FIG. 1 is provided with a substrate 1, such as glass, and a protective film 2 having moisture resistance for protecting the TFT element or the organic compound layer on the substrate 1. The reference numeral 3 denotes a metal gate electrode 3. The reference numeral 4 denotes a gate insulation film 4 and the reference numeral 5 denotes a semiconductor layer.

A TFT element 8 has a semiconductor layer 5, a drain electrode 6, and a source electrode 7. An insulation film 9 is provided on the TFT element 8. An anode 11 of the organic light emitting device and the source electrode 7 are connected through a contact hole 10. The configuration of the display device is not limited to the configuration and either one of the anode or the cathode may be connected to either one of the source electrode or the drain electrode of the TFT element.

In the display device 20 of FIG. 1, an organic compound layer 12 is illustrated in such a manner that an organic compound layer of a single layer structure or a multilayer structure forms one layer. On a cathode 13, a first protective layer 14 and a second protective layer 15 for suppressing degradation of the organic light emitting device are provided.

In the display device according to this embodiment, an MIM element may be used as a switching element in place of the transistor. The transistor is not limited to a transistor employing a single crystal silicon wafer and may be a thin film transistor having an active layer on an insulating surface of a substrate. A thin film transistor containing single crystal silicon as an active layer, a thin film transistor containing non-single crystal silicon, such as amorphous silicon or microcrystalline silicon, as an active layer, and a thin film transistor containing non-single crystal oxide semiconductor, such as IZO (indium zinc oxide) or IGZO (indium gallium zinc oxide), as an active layer may be acceptable. The thin film transistor is also referred to as a TFT element.

EXAMPLES

Hereinafter, the invention is described with reference to Examples. However, the invention is not limited thereto.

Example 1

Synthesis of Exemplary Compound A2

[Chem. 12]

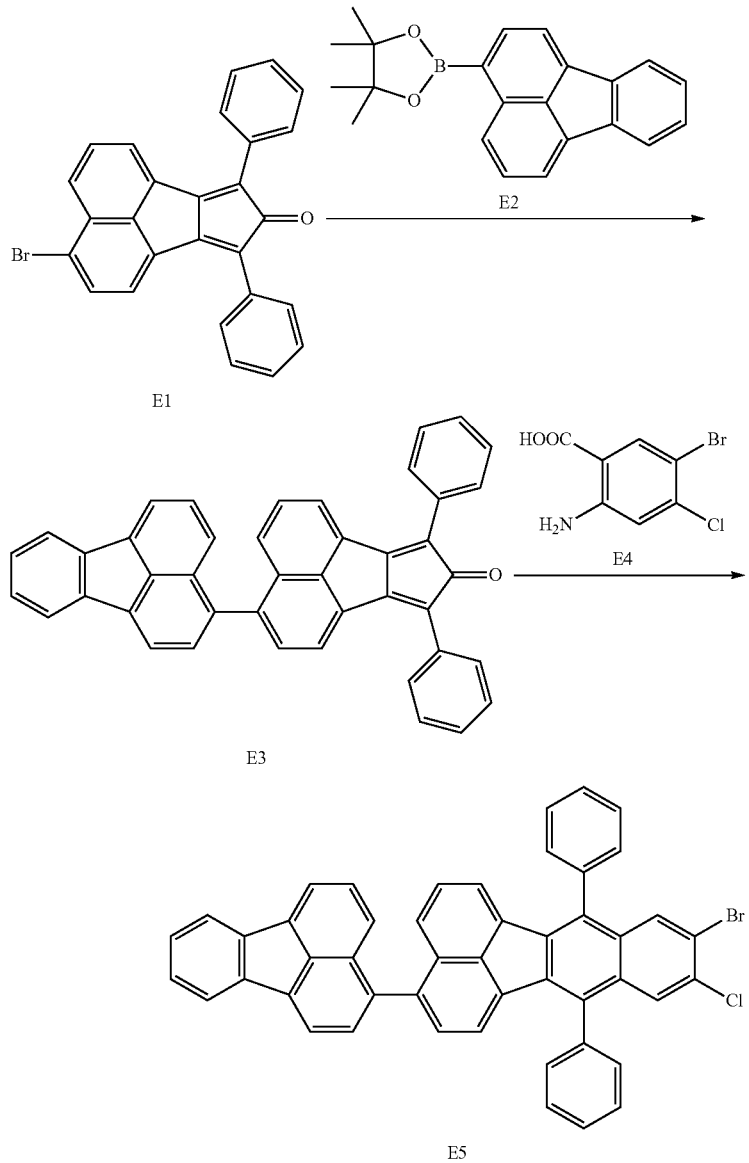

(1) Synthesis of Compound E3

The following reagents and solvent were charged in a 200 ml eggplant flask.
Compound E1: 4.35 g (10 mmol)
Compound E2: 3.28 g (10 mmol)
Pd(PPh$_3$)$_4$: 0.2 g
Toluene: 50 ml
Ethanol: 20 ml
2M-sodium carbonate solution: 50 ml Next, the reaction solution was heated to 80° C. under nitrogen flow, and stirred at this temperature (80° C.) for 6 hours. After the end of the reaction, water was added for liquid separation, dissolved in chloroform, purified by column chromatography (chloroform), and then re-crystallized with chloroform/methanol, thereby obtaining 4.17 g (yield: 75%) of a dark green compound E3.

(2) Synthesis of Compound E5

The following reagents and solvent were charged in a 100 ml eggplant flask.
Compound E3: 3.90 g (7 mmol)
Compound E4: 2.25 g (9 mmol)
Isoamyl nitrite: 1.05 g (9 mmol)
Toluene: 40 ml Next, the reaction solution was heated to 110° C. under nitrogen flow, and stirred at this temperature (110° C.) for 3 hours. After the end of the reaction, the resultant substance was washed with 40 ml of water twice. The obtained organic layer was washed with a saturated sodium chloride solution, and then dried over magnesium sulfate. The solution was filtered, and then the filtrate was condensed to thereby obtain a dark brown liquid. The liquid was purified by column chromatography (chloroform/heptane=1:4), and then re-crystallized with chloroform/methanol, thereby obtaining 4.27 g (yield: 85%) of a yellow crystal E5.

[Chem. 13]

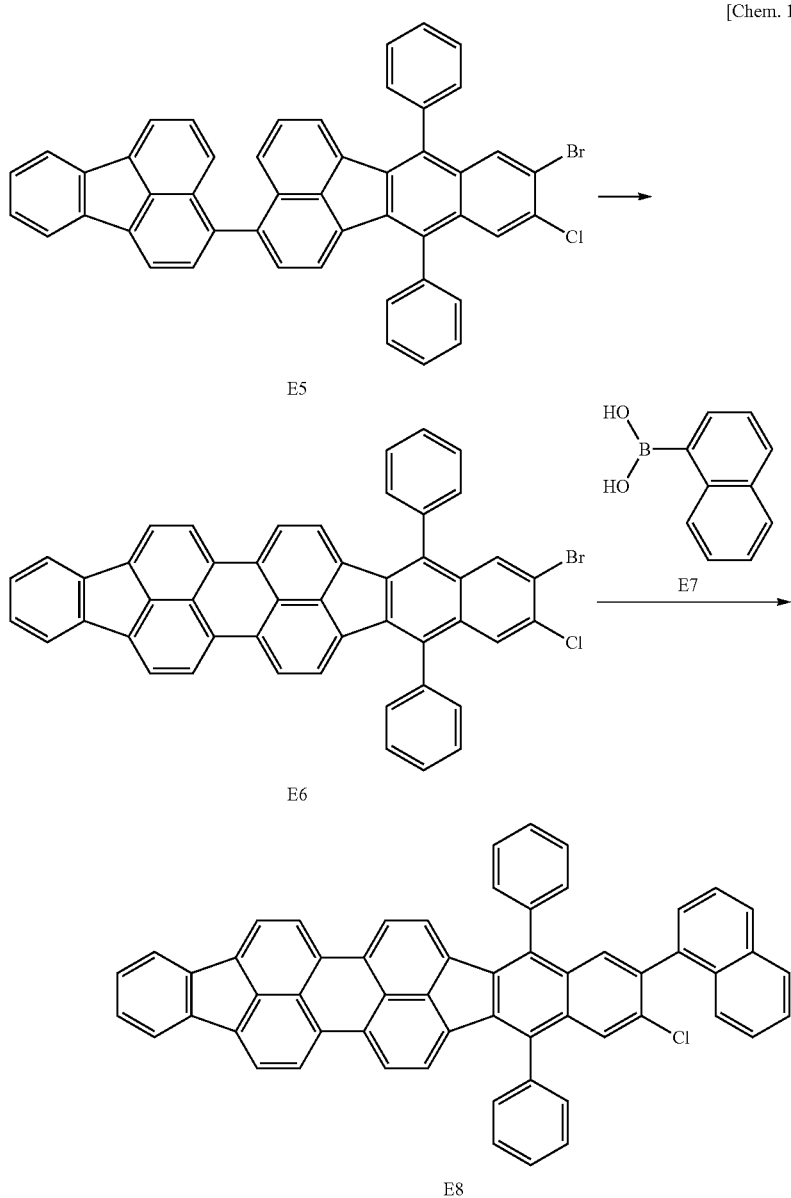

(3) Synthesis of Compound E6

The following reagents and solvent were charged in a 500 ml reactor.
Compound E5: 3.59 g (5 mmol)
Trifluoroacetic acid: 30 ml
Methylene chloride: 300 ml
Next, the following reagent was put in the reactor under water bathing.

BF$_3$.OEt: 9 ml
Next, the reaction solution was stirred for about 10 minutes, and then, 2.5 g of DDQ (2,3-dichloro-5,6-dicyano-p-benzoquinone, 11 mmol) was put in the solution. Next, the reaction solution was stirred for 10 minutes, and then 2.1 g (11 mmol) of ferrocene was put in under 20° C. water bathing. After stirring for about 5 minutes, 300 ml of methanol was added. By filtering a red precipitate formed at this time, a red solid was obtained. Next, the solid was dissolved in chlorobenzene, and then re-crystallized with heptane, thereby obtaining 3.2 g (yield: 90%) of a red crystalline exemplary compound E6.

(4) Synthesis of Compound E8

The following reagents and solvent were charged in a 200 ml eggplant flask.
Compound E6: 2.15 g (3 mmol)
Compound E7: 0.57 g (3.3 mmol)
Pd(PPh$_3$)$_4$: 0.6 g
Toluene: 100 ml
Ethanol: 10 ml
2M-sodium carbonate solution: 30 ml Next, the reaction solution was heated to 80° C. under nitrogen flow, and stirred at this temperature (80° C.) for 8 hours. After the end of the reaction, ethanol was added to precipitate crystals, the crystals were filtered off, and then the crystals were successively washed with water, ethanol, and heptane. Next, the obtained crystals were dissolved in chlorobenzene by heating, the hot solution was filtered, and then re-crystallization was performed, thereby obtaining 1.76 g (yield: 77%) of a red compound E8.

[Chem. 14]

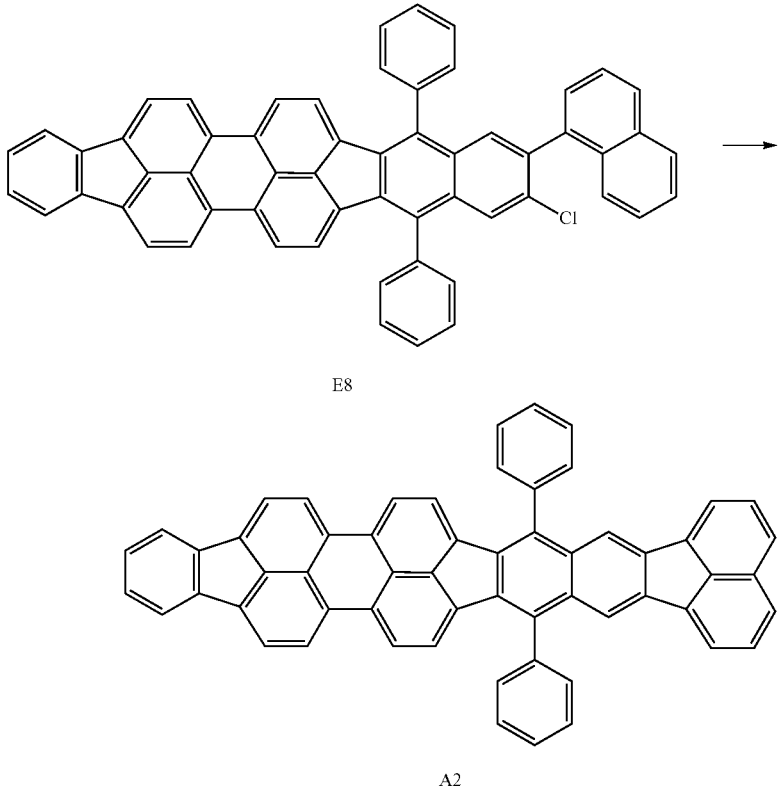

(5) Synthesis of Exemplary Compound A2

The following reagents and solvent were charged in a 20 ml eggplant flask.
Compound E8: 763 mg (1 mmol)
Pd(dba)$_2$: 238 mg
P(Cy)$_2$(tricyclohexylphosphine): 280 mg
DBU (diazabicycloundecene): 0.15 ml
DMF: 5 ml Next, the reaction solution was heated to 145° C. under nitrogen flow, and stirred at this temperature (145° C.) for 6 hours. After the end of the reaction, ethanol was added to precipitate crystals, the crystals were filtered off, and then the crystals were successively washed with water, ethanol, and heptane. Next, the obtained purple crystals were dissolved in toluene by heating, the hot solution was filtered, and then re-crystallization was performed with toluene/methanol, thereby obtaining 0.57 g (yield: 78%) of a dark red exemplary compound A2.

The purity of this compound was confirmed using HPLC to be 99% or more.

With respect to the light emission spectrum of the toluene solution in 1×10$^{-5}$ mol/L of the exemplary compound A2, the photoluminescence at an excitation wavelength of 360 nm was measured using F-4500 manufactured by Hitachi, and then the spectrum having the maximum intensity at 595 nm was obtained.

The exemplary compound A2 was subjected to mass spectrometry using MALDI-TOF-MS (Autoflex LRF manufactured by Bruker).
[MALDI-TOF-MS]
Actual measurement value: m/z=725.88, Calculated value: $C_{58}H_{30}$=726.23

Example 2

Synthesis of Exemplary Compound A7

An exemplary compound A7 was obtained in the same manner as in Example 1, except using the compound E9 shown below in place of the compound E1 and the compound E10 shown below in place of the compound E2 in Example 1(1).

[Chem. 15]

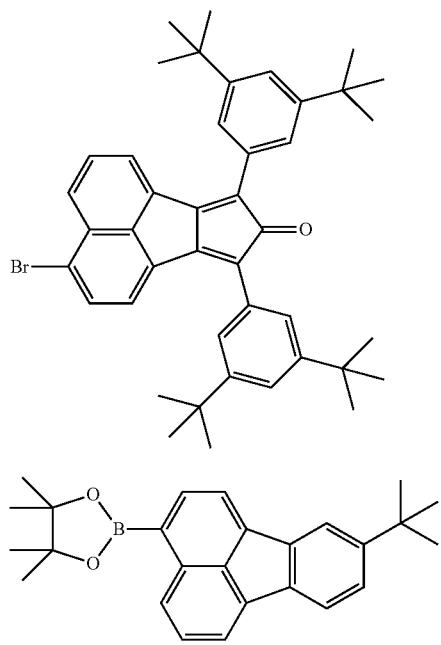

The purity of the obtained compound was confirmed using HPLC to be 98% or more.

The light emission spectrum in the toluene solution (Concentration: $1\times10^{-5}$ mol/L) of the exemplary compound A7 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=1006.42, Calculated value: $C_{78}H_{70}$=1006.55

Example 3

Synthesis of Exemplary Compound A8

An exemplary compound A8 was obtained in the same manner as in Example 1, except using the compound E11 shown below in place of the compound E1 and the compound E12 shown below in place of the compound E2 in Example 1(1) and the compound E13 shown below in place of the compound E7 in Example 1(4).

[Chem. 16]

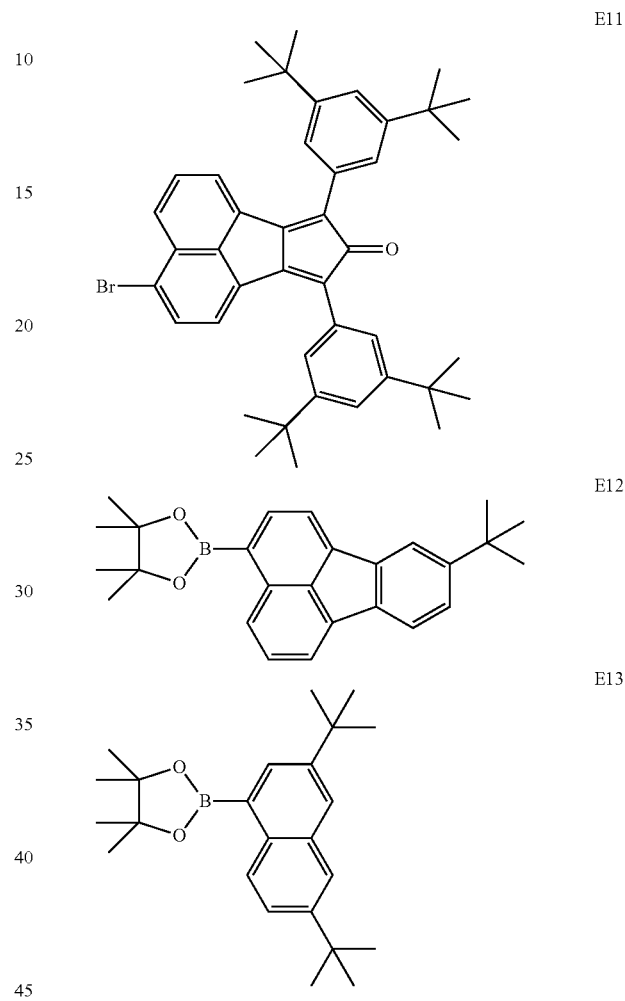

The purity of the obtained compound was confirmed using HPLC to be 98% or more.

The light emission spectrum in the toluene solution (Concentration: $1\times10^{-5}$ mol/L) of the exemplary compound A8 was measured in the same manner as in Example 1, and, as a result, the spectrum having the maximum intensity at 598 nm was obtained.

The mass spectrometry was performed using MALDI-TOF-MS (Autoflex LRF manufactured by Bruker).
[MALDI-TOF-MS]
Actual measurement value: m/z=1117.89, Calculated value: $C_{86}H_{86}$=1118.67

Example 4

Synthesis of Exemplary Compound A18

An exemplary compound A18 was obtained in the same manner as in Example 1, except using the compound E14 shown below in place of the compound E1 and the compound E15 shown below in place of the compound E2.

[Chem. 17]

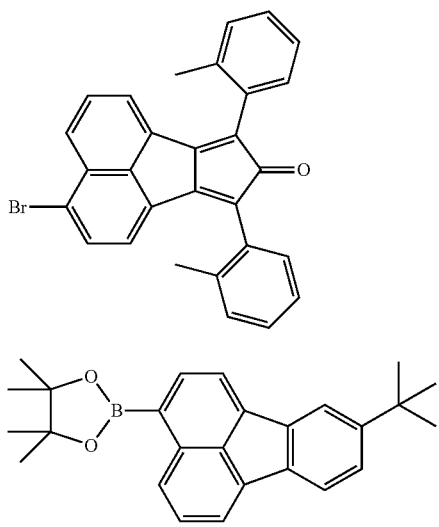

E14

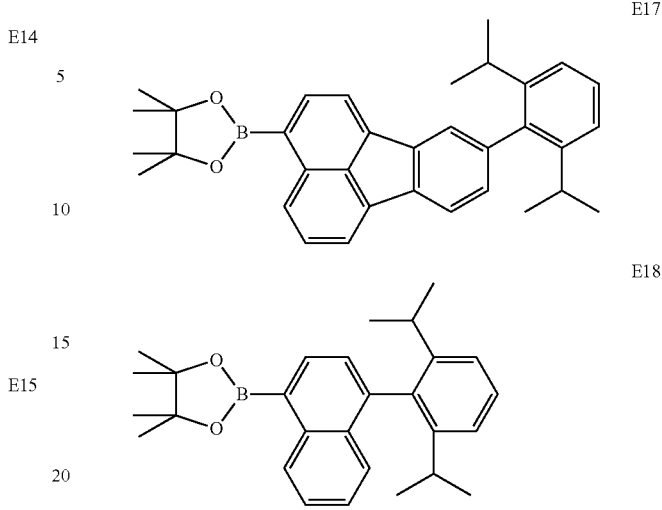

E17

E18

The purity of the obtained compound was confirmed using HPLC to be 97% or more.

The light emission spectrum in the toluene solution (Concentration: 1×10$^{-5}$ mol/L) of the exemplary compound A18 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=810.02, Calculated value: C$_{64}$H$_{42}$=810.33

Example 5

Synthesis of Exemplary Compound A25

An exemplary compound A25 was obtained in the same manner as in Example 1, except using the compound E16 shown below in place of the compound E1 and the compound E17 shown below in place of the compound E2 in Example 1(1) and the compound E18 shown below in place of the compound E7 in Example 1(4).

[Chem. 18]

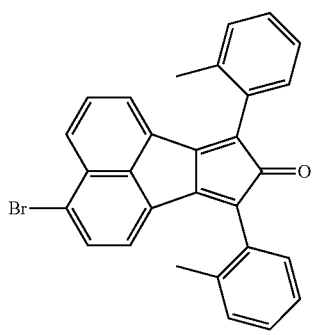

E16

The purity of the obtained compound was confirmed using HPLC to be 98% or more.

The light emission spectrum in the toluene solution (Concentration: 1×10$^{-5}$ mol/L) of the exemplary compound A25 was measured in the same manner as in Example 1, and, as a result, the spectrum having the maximum intensity at 599 nm was obtained.

The mass spectrometry was performed using MALDI-TOF-MS (Autoflex LRF manufactured by Bruker).
[MALDI-TOF-MS]
Actual measurement value: m/z=1074.11, Calculated value: C$_{84}$H$_{66}$=1074.52

Example 6

Synthesis of Exemplary Compound A26

An exemplary compound A26 was obtained in the same manner as in Example 1, except using the compound E19 shown below in place of the compound E1 and the compound E20 shown below in place of the compound E2 in Example 1(1).

[Chem. 19]

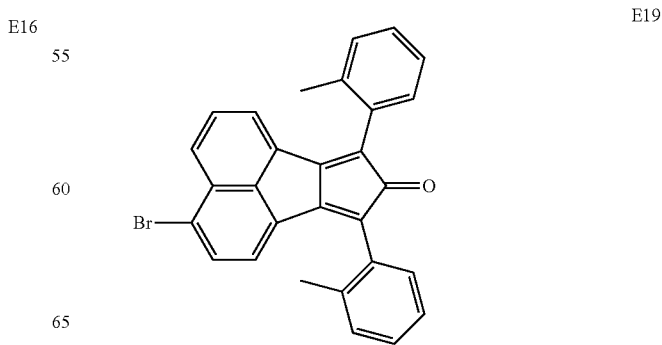

E19

-continued

E20
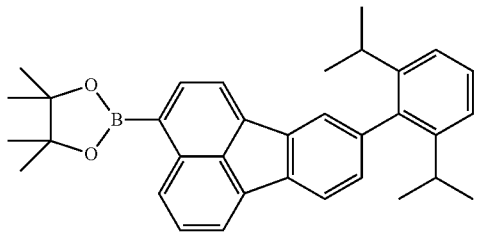

The purity of the obtained compound was confirmed using HPLC to be 98% or more.

The light emission spectrum in the toluene solution (Concentration: $1\times10^{-5}$ mol/L) of the exemplary compound A26 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=913.88, Calculated value: $C_{72}H_{50}$=914.39

Example 7

Synthesis of Exemplary Compound A31

An exemplary compound A31 was obtained in the same manner as in Example 1, except using the compound E21 shown below in place of the compound E2 in Example 1(1) and the compound E22 shown below in place of the compound E7 in Example 1(4).

[Chem. 20]

E21
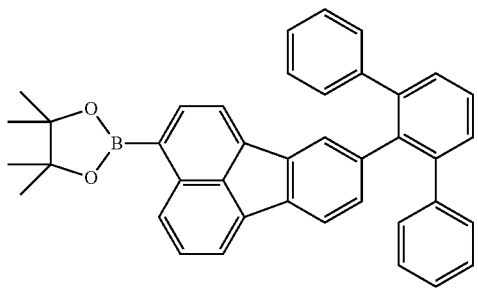

E22
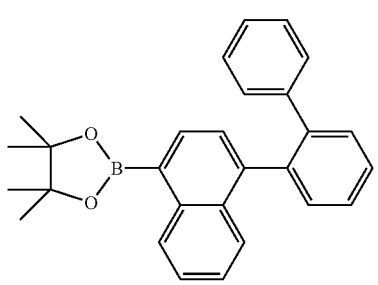

The purity of the obtained compound was confirmed using HPLC to be 98% or more.

The light emission spectrum in the toluene solution (Concentration: $1\times10^{-5}$ mol/L) of the exemplary compound A31 was measured in the same manner as in Example 1, and, as a result, the spectrum having the maximum intensity at 602 nm was obtained.

The mass spectrometry was performed using MALDI-TOF-MS (Autoflex LRF manufactured by Bruker).
[MALDI-TOF-MS]
Actual measurement value: m/z=1106.05, Calculated value: $C_{88}H_{50}$=1106.39

Example 8

Synthesis of Exemplary Compound B2

An exemplary compound B2 was obtained in the same manner as in Example 1, except using the compound E23 shown below in place of the compound E1 in Example 1(1).

[Chem. 21]

E23
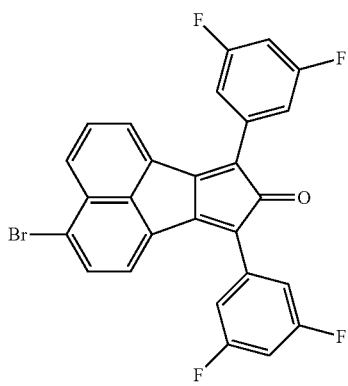

The purity of the obtained compound was confirmed using HPLC to be 97% or more.

The light emission spectrum in the toluene solution (Concentration: $1\times10^{-5}$ mol/L) of the exemplary compound B2 was measured in the same manner as in Example 1, and, as a result, the spectrum having the maximum intensity at 595 nm was obtained.

The mass spectrometry was performed using MALDI-TOF-MS (Autoflex LRF manufactured by Bruker).
[MALDI-TOF-MS]
Actual measurement value: m/z=797.98, Calculated value: $C_{58}H_{26}F_{4}$=798.20

Example 9

Synthesis of Exemplary Compound B7

An exemplary compound B7 was obtained in the same manner as in Example 1, except using the compound E24 shown below in place of the compound E1 in Example 1(1) and the compound E25 shown below in place of the compound E7 in Example 1(4).

[Chem. 22]

E24
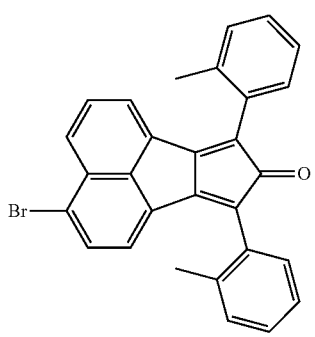

-continued

E25

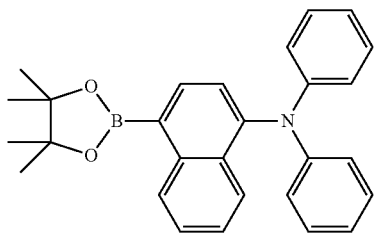

The purity of the obtained compound was confirmed using HPLC to be 98% or more.

The light emission spectrum in the toluene solution (Concentration: $1\times10^{-5}$ mol/L) of the exemplary compound B7 was measured in the same manner as in Example 1, and, as a result, the spectrum having the maximum intensity at 600 nm was obtained.

The mass spectrometry was performed using MALDI-TOF-MS (Autoflex LRF manufactured by Bruker).

[MALDI-TOF-MS]

Actual measurement value: m/z=921.01, Calculated value: $C_{72}H_{43}N$=921.34

Example 10

In this example, an organic light emitting device was produced in which an anode, a hole transporting layer, an electron blocking layer, a light emitting layer, a hole/exciton blocking layer, an electron transporting layer, and a cathode were successively formed on a substrate. Hereinafter, some of the materials used in this example are shown.

[Chem. 23]

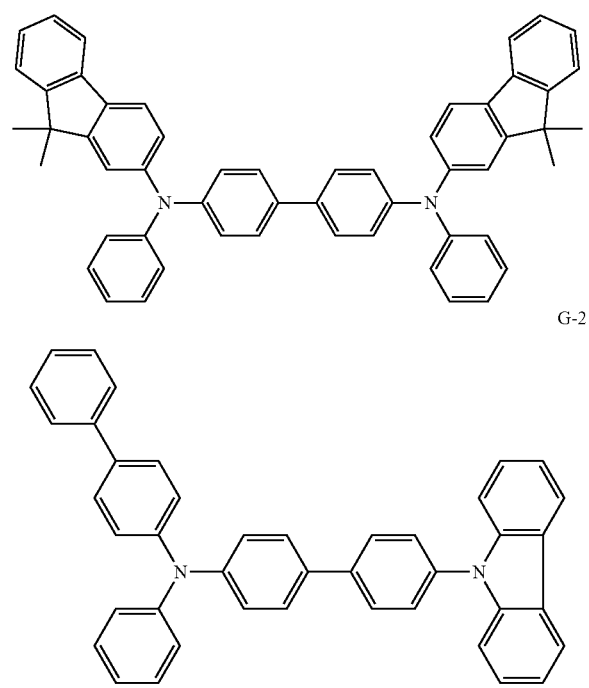

First, an ITO was formed into a film, and then subjected to desired patterning processing to thereby form an ITO electrode (anode) on a glass substrate. In this case, the film thickness of the ITO electrode was set to 100 nm. The substrate on which the ITO electrode was formed as described above was used as an ITO substrate in the following process.

The organic compound layers and the electrode layers shown in Table 3 were successively formed on the ITO substrate. In this case, the electrode area of the electrodes (a metal electrode layer and a cathode) facing each other was set to 3 mm².

TABLE 3

| Material | | Film thickness (nm) |
| --- | --- | --- |
| Hole transporting layer | G-1 | 30 |
| Electron blocking layer | G-2 | 10 |
| Light emitting layer | G-3 (Host) | 30 |
| | G-4 (Assist) | |
| | Exemplary compound A7 (Guest) | |
| | (G-3:G-4:A7 = 60:39.5:0.5 (Weight ratio)) | |
| Hole blocking layer | G-5 | 10 |
| Electron transporting layer | G-6 | 30 |
| First metal electrode layer | LiF | 1 |
| Second metal electrode layer | Al | 100 |

In this example, G-3 and G-4 are H6 and H23 shown in Table 2, respectively.

The obtained device was measured and evaluated for the characteristics of the device. The maximum light emission wavelength of the light emitting device was 611 nm and the chromaticity was (X, Y)=(0.66, 0.33). With respect to a measurement device, specifically, the current-voltage characteristics were measured with a microammeter 4140B manufactured by Hewlett-Packard Company and the light emission luminosity was measured with BM7 manufactured by TOPCON CORPORATION. The measurements results are shown in Table 4.

Examples 11 to 20

Organic light emitting devices were produced in the same manner as in Example 10, except changing, as appropriate, G-3, G-4, and the guest in Example 10 to the compounds shown in Table 4. The obtained devices were measured and evaluated for the characteristics in the same manner as in Example 10. The measurement results are shown in Table 4. In Table 4, when the materials of G-3 and G-4 are the same, the materials of the host and the assist are the same and the hosts shown in Table 2 were used.

TABLE 4

|  | Guest | G-3 | G-4 | Luminous efficiency (cd/A) | Voltage (V) |
|---|---|---|---|---|---|
| Example 10 | A7 | H6 | H23 | 5.7 | 3.9 |
| Example 11 | A7 | H19 | H19 | 5.9 | 4.0 |
| Example 12 | A8 | H12 | H21 | 6.1 | 4.0 |
| Example 13 | A9 | H19 | H24 | 6.0 | 4.1 |
| Example 14 | A17 | H9 | H19 | 5.5 | 4.1 |
| Example 15 | A18 | H19 | H23 | 5.7 | 4.2 |
| Example 16 | A22 | H12 | H21 | 6.2 | 3.8 |
| Example 17 | A25 | H18 | H19 | 6.3 | 4.0 |
| Example 18 | A26 | H19 | H19 | 6.0 | 3.8 |
| Example 19 | A34 | H10 | H23 | 5.8 | 4.2 |
| Example 20 | B2 | H16 | H21 | 6.3 | 3.9 |

Example 21

In this example, an organic light emitting device was produced in which an anode, a hole injecting layer, a hole transporting layer, a light emitting layer, an electron transporting layer, an electron injecting layer, and a cathode were successively formed on a substrate. The organic light emitting device produced in this example has a resonance structure. Hereinafter, some of the materials used in this example are shown.

[Chem. 24]

G-11

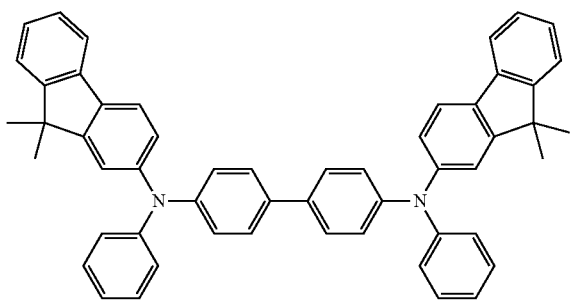

G-12

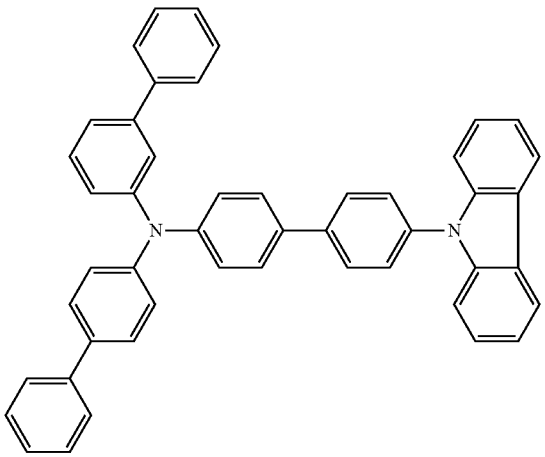

G-15

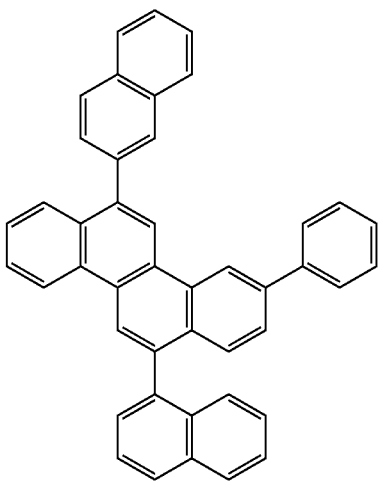

G-16

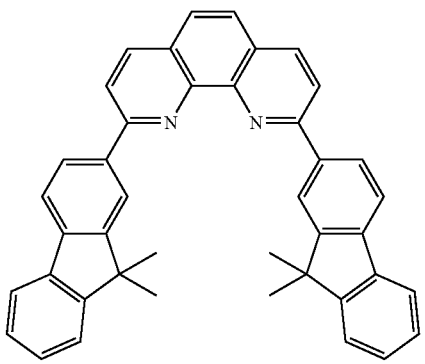

First, aluminum alloy (AlNd) was formed into a film by a sputtering method to form a reflective anode on a glass substrate (support). In this case, the film thickness of the reflective anode was set to 100 nm. Next, ITO was formed into a film by a sputtering method on the reflective anode to form a transparent anode. In this case, the film thickness of the transparent anode was set to 80 nm. Next, an acryl element isolation film was formed around the anode with a film thickness of 1.5 μm, and then subjected to desired patterning and molding to thereby provide an opening portion having a radius of 3 mm. Next, the substrate on which the anode was formed was successively ultrasonically cleaned with acetone and isopropyl alcohol (IPA). Next, the substrate was cleaned by boiling with IPA, and then dried. Next, the substrate surface was subjected to UV/ozone washing.

Next, vacuum deposition by resistance heating in a vacuum chamber of $1\times10^{-5}$ Pa was performed to successively form the organic compound layers shown in Table 5 on the ITO substrate.

TABLE 5

| | Material | Film thickness (nm) |
|---|---|---|
| Hole transporting layer | G-11 | 135 |
| Electron blocking layer | G-12 | 10 |
| Light emitting layer | G-13 (Host) G-14 (Assist) Exemplary compound A18 (Guest) (G-13:G-14:A18 = 60:3905:0.5 (Weight ratio)) | 30 |
| Electron transporting layer | G-15 | 10 |
| Electron injecting layer | G-16 Li (G-16:Li = 80:20( )) | 70 |

In this example, G-13 and G-14 are H10 and H19 shown in Table 2, respectively.

Next, ITO was formed into a film by a sputtering method to form a cathode on the electron injecting layer. In this case, the film thickness of the cathode was set to 30 nm. Finally, sealing was performed under a nitrogen atmosphere.

Thus, an organic light emitting device was produced.

The obtained device was measured and evaluated for the characteristics of the device. Specifically, the current-voltage characteristics were measured with a microammeter 4140B manufactured by Hewlett-Packard Company and the light emission luminosity was measured with BM7 manufactured by TOPCON CORPORATION. The measurements results are shown in Table 6.

Examples 22 to 25

Organic light emitting devices were produced in the same manner as in Example 21, except changing, as appropriate, G-13, G-14, and the guest in Example 21 to the compounds shown in Table 6. The obtained devices were measured and evaluated for the characteristics in the same manner as in Example 21. The measurement results are shown in Table 6. In Table 6, when the materials of G-13 and G-14 are the same, the materials of the host and the assist are the same and the hosts shown in Table 2 were used.

TABLE 6

| | Guest | G-13 | G-14 | Luminous efficiency (cd/A) | Voltage (V) |
|---|---|---|---|---|---|
| Example 21 | A17 | H10 | H19 | 10.1 | 4.5 |
| Example 22 | A3 | H12 | H21 | 9.1 | 4.6 |
| Example 23 | A7 | H10 | H23 | 10.3 | 4.4 |
| Example 24 | A18 | H19 | H19 | 9.8 | 4.5 |
| Example 25 | A34 | H18 | H23 | 10.2 | 4.5 |

Example 26

In this example, an organic light emitting device was produced in which an anode, a hole transporting layer, a first light emitting layer, a second light emitting layer, a hole/exciton blocking layer, an electron transporting layer, and a cathode were successively formed on a substrate. The organic light emitting device of this example has an aspect in which a plurality of light emitting layers are provided. Hereinafter, some of the materials used in this example are shown.

[Chem. 25]

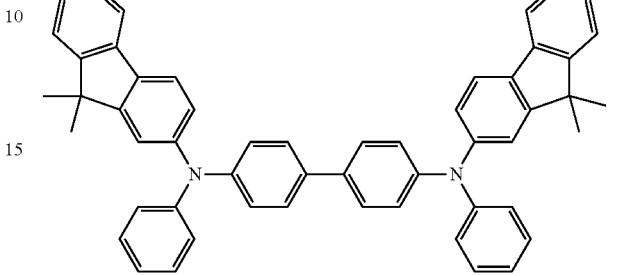

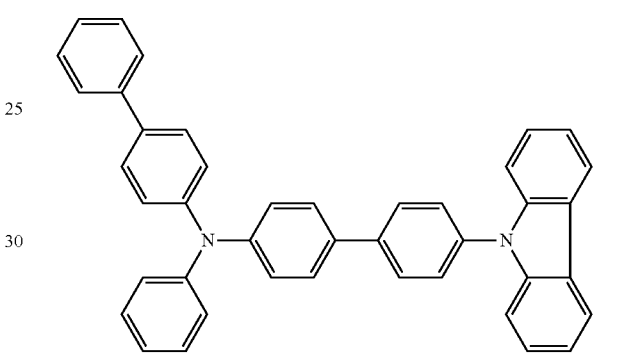

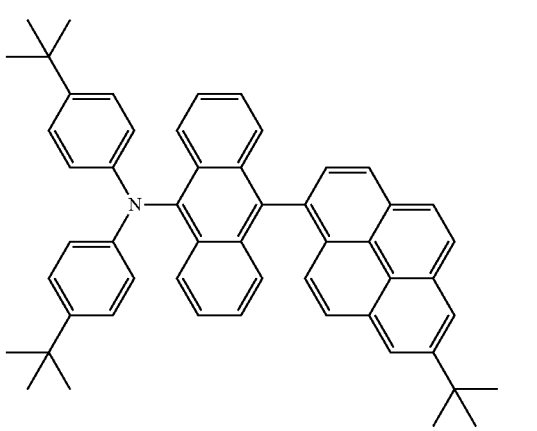

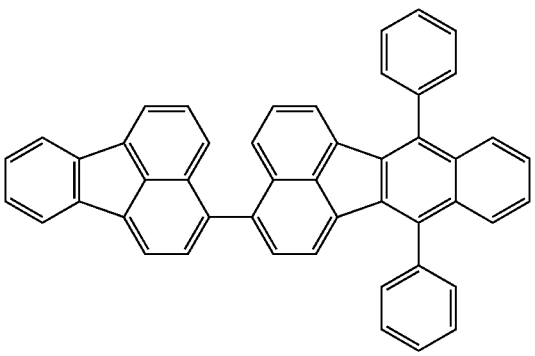

-continued

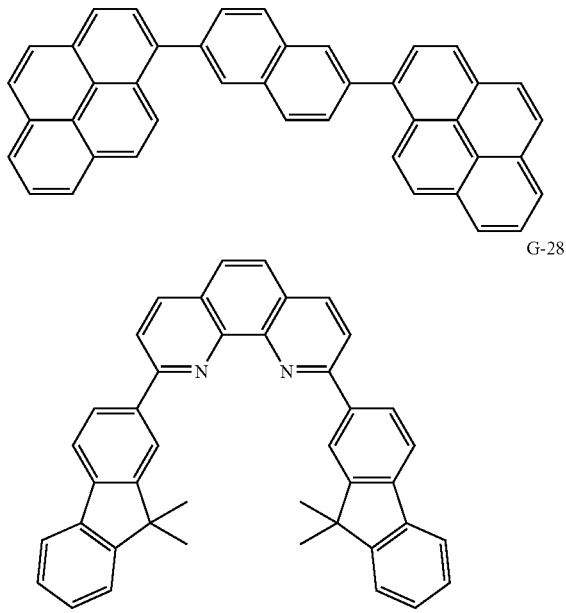

G-27

G-28

First, an ITO was formed into a film, and then subjected to desired patterning processing to thereby form an ITO electrode (anode) on a glass substrate. In this case, the film thickness of the ITO electrode was set to 100 nm. The substrate on which the ITO electrode was formed as described above was used as an ITO substrate in the following process.

Next, vacuum deposition by resistance heating in a vacuum chamber of $1\times10^{-5}$ Pa was performed to successively form the organic compound layers and the electrode layers shown in Table 7 on the ITO substrate. In this case, the electrode area of the electrodes (a metal electrode layer and a cathode) facing each other was set to 3 mm².

TABLE 7

| Material | | Film thickness (nm) |
|---|---|---|
| Hole transporting layer | G-21 | 30 |
| Electron blocking layer | G-22 | 10 |
| First light emitting layer | G-23 (First host) | 20 |
| | G-24 (First guest) | |
| | Exemplary compound A11 | |
| | (Second guest) | |
| | (G-23:G-24:A11 = | |
| | 60:39.5:0.5 (Weight ratio)) | |
| Second light emitting layer | G-25 (Second host) | 20 |
| | G-26 (Third host) | |
| | (G-25:G-26 = 96:4 | |
| | (Weight ratio)) | |
| Hole blocking layer | G-27 | 10 |
| Electron transporting layer | G-28 | 30 |
| First metal electrode layer | LiF | 1 |
| Second metal electrode layer | Al | 100 |

In this example, G-23 and G-25 are H19 and H4 shown in Table 2, respectively.

The obtained device was measured and evaluated for the characteristics of the device. Specifically, the current-voltage characteristics were measured with a microammeter 4140B manufactured by Hewlett-Packard Company and the light emission luminosity was measured with BM7 manufactured by TOPCON CORPORATION. The measurements results are shown in Table 8.

Examples 27 to 29

Organic light emitting devices were produced in the same manner as in Example 26, except changing, as appropriate, G-22, G-25, and the guest in Example 26 to the compounds shown in Table 8. The obtained devices were measured and evaluated for the characteristics of the device in the same manner as in Example 26. The measurements results are shown in Table 8. G-22 and G-25 used in Table 8 are the hosts shown in Table 2.

TABLE 8

| | Guest | G-23 | G-25 | Luminous efficiency (cd/A) | Voltage (V) |
|---|---|---|---|---|---|
| Example 26 | A11 | H19 | H4 | 13.1 | 5.2 |
| Example 27 | A14 | H18 | H4 | 12.5 | 5.3 |
| Example 28 | A27 | H22 | H7 | 13.3 | 5.7 |
| Example 29 | A33 | H11 | H10 | 11.8 | 5.3 |

Thus, as described with reference to the examples, when the organic compound according to the invention is used for a light emitting device, the organic compound according to the invention exhibits a chromaticity suitable for red light emission by increasing the wavelength by about 10 nm to the maximum light emission wavelength in the toluene diluted solution. More specifically, the organic compound of this embodiment is suitable as a red light emitting material in a light emitting device. As the luminous efficiency, a high value, 10.3 cd/A at the maximum, is indicated when only the compound of the invention is used for the light emitting material.

Example 30

Synthesis of Exemplary Compound A3

An exemplary compound A3 was obtained in the same manner as in Example 1, except using the compound E26 shown below in place of the compound E1 in Example 1(1).

[Chem. 26]

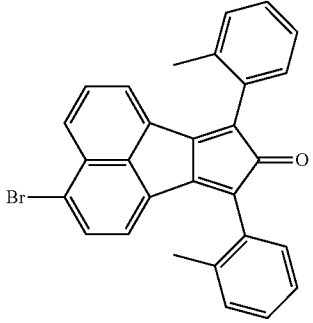

E26

The purity of the obtained compound was confirmed using HPLC to be 98% or more.

The light emission spectrum in the toluene solution (Concentration: $1\times10^{-5}$ mol/L) of the exemplary compound A3 was measured in the same manner as in Example 1, and, as a result, the spectrum having the maximum intensity at 596 nm was obtained.

The mass spectrometry was performed using MALDI-TOF-MS (Autoflex LRF manufactured by Bruker).
[MALDI-TOF-MS]
Actual measurement value: m/z=754.18, Calculated value: $C_{64}H_{34}$=754.27

Example 31

Synthesis of Exemplary Compound A37

An exemplary compound A37 was obtained in the same manner as in Example 1, except using the compound E27 shown below in place of the compound E7 in Example 1(4).

[Chem. 27]

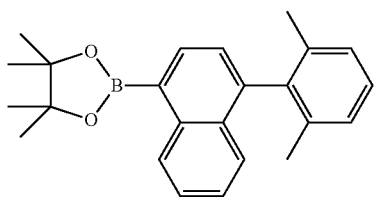

E27

The purity of the obtained compound was confirmed using HPLC to be 98% or more.

The light emission spectrum in the toluene solution (Concentration: $1 \times 10^{-5}$ mol/L) of the exemplary compound A37 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=830.40, Calculated value: $C_{66}H_{38}$=830.30

Example 32

Synthesis of Exemplary Compound A39

An exemplary compound A39 was obtained in the same manner as in Example 1, except using the compound E28 shown below in place of the compound E2 in Example 1(1).

[Chem. 28]

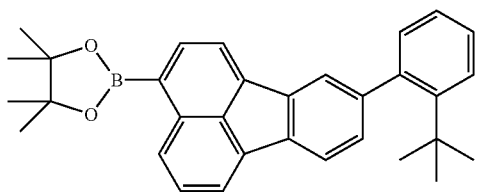

E28

The purity of the obtained compound was confirmed using HPLC to be 97% or more.

The light emission spectrum in the toluene solution (Concentration: $1 \times 10^{-5}$ mol/L) of the exemplary compound A9 was measured in the same manner as in Example 1, and, as a result, the spectrum having the maximum intensity at 596 nm was obtained.

The mass spectrometry was performed using MALDI-TOF-MS (Autoflex LRF manufactured by Bruker).
[MALDI-TOF-MS]
Actual measurement value: m/z=858.92, Calculated value: $C_{68}H_{42}$=858.33

Example 33

Synthesis of Exemplary Compound A46

An exemplary compound A46 was obtained in the same manner as in Example 1, except using the compound E29 shown below in place of the compound E1 in Example 1(1) and the compound E30 shown below in place of the compound E7 in Example 1(4).

[Chem. 29]

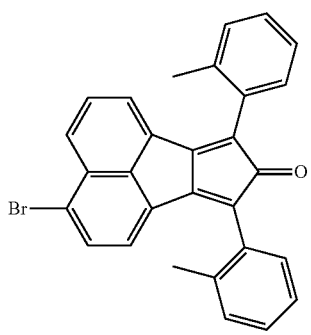

E29

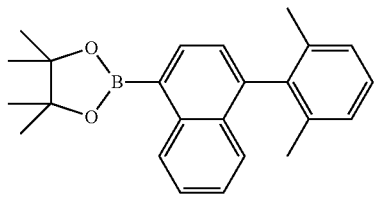

E30

The purity of the obtained compound was confirmed using HPLC to be 98% or more.

The light emission spectrum in the toluene solution (Concentration: $1 \times 10^{-5}$ mol/L) of the exemplary compound A46 was measured in the same manner as in Example 1, and, as a result, the spectrum having the maximum intensity at 596 nm was obtained.

The mass spectrometry was performed using MALDI-TOF-MS (Autoflex LRF manufactured by Bruker).
[MALDI-TOF-MS]
Actual measurement value: m/z=858.56, Calculated value: $C_{68}H_{42}$=858.33

Example 34

Synthesis of Exemplary Compound A47

An exemplary compound A47 was obtained in the same manner as in Example 1, except using the compound E31 shown below in place of the compound E1 in Example 1(1) and the compound E32 shown below in place of the compound E7 in Example 1(4).

[Chem. 30]

E31
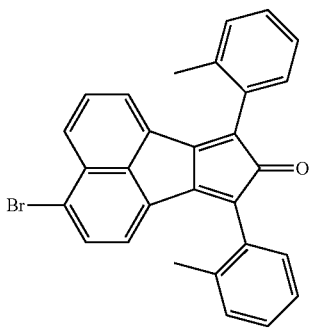

E32
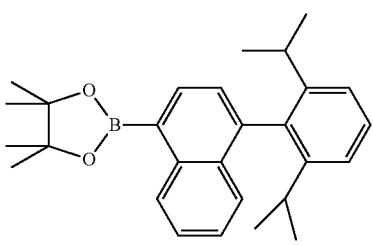

The purity of the obtained compound was confirmed using HPLC to be 98% or more.

The light emission spectrum in the toluene solution (Concentration: $1\times10^{-5}$ mol/L) of the exemplary compound A47 was measured in the same manner as in Example 1, and, as a result, the spectrum having the maximum intensity at 596 nm was obtained.

The mass spectrometry was performed using MALDI-TOF-MS (Autoflex LRF manufactured by Bruker).
[MALDI-TOF-MS]
Actual measurement value: m/z=913.23, Calculated value: $C_{72}H_{50}$=914.39

Example 35

Synthesis of Exemplary Compound A48

An exemplary compound A48 was obtained in the same manner as in Example 1, except using the compound E33 shown below in place of the compound E1 and the compound E34 shown below in place of the compound E2 in Example 1(1).

[Chem. 31]

E33
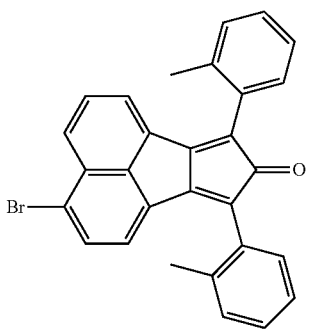

E34
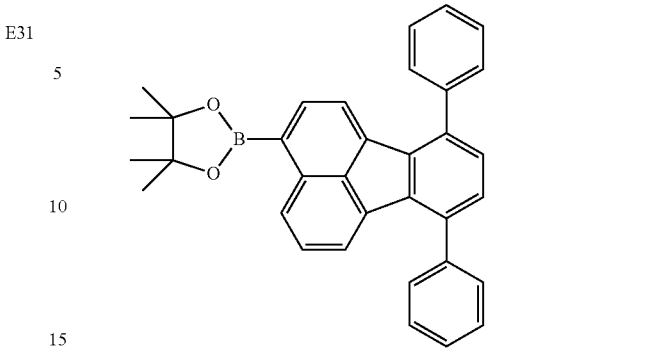

The purity of the obtained compound was confirmed using HPLC to be 97% or more.

The light emission spectrum in the toluene solution (Concentration: $1\times10^{-5}$ mol/L) of the exemplary compound A48 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=906.67, Calculated value: $C_{72}H_{42}$=906.33

Example 36

Synthesis of Exemplary Compound A52

An exemplary compound A52 was obtained in the same manner as in Example 1, except using the compound E35 shown below in place of the compound E1 and the compound E36 shown below in place of the compound E2 in Example 1(1).

[Chem. 32]

E35
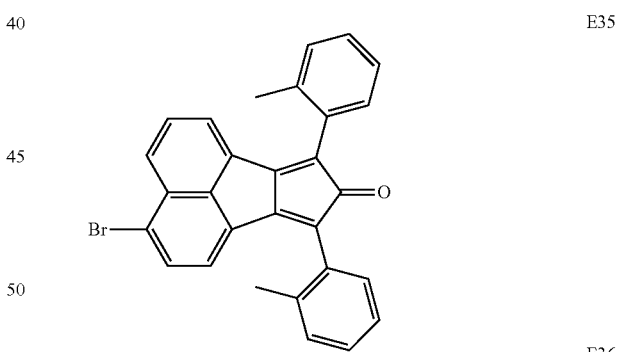

E36
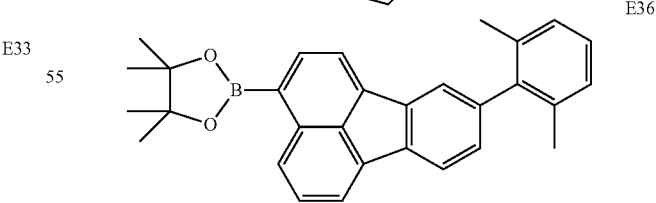

The purity of the obtained compound was confirmed using HPLC to be 98% or more.

The light emission spectrum in the toluene solution (Concentration: $1\times10^{-5}$ mol/L) of the exemplary compound A52 was measured in the same manner as in Example 1, and, as a result, the spectrum having the maximum intensity at 597 nm was obtained.

The mass spectrometry was performed using MALDI-TOF-MS (Autoflex LRF manufactured by Bruker).
[MALDI-TOF-MS]
Actual measurement value: m/z=858.65, Calculated value: $C_{68}H_{42}$=858.33

Examples 37 to 47

Organic light emitting devices were produced in the same manner as in Example 10, except changing, as appropriate, G-3, G-4, and the guest in Example 10 to the compounds shown in Table 4. The obtained devices were measured and evaluated for the characteristics in the same manner as in Example 27. The measurement results are shown in the following table. In the following table, when the materials of G-3 and G-4 are the same, the materials of the host and the assist are the same and the hosts shown in Table 2 were used.

TABLE 9

|  | Guest | G-3 | G-4 | Luminous efficiency (cd/A) | Voltage (V) |
| --- | --- | --- | --- | --- | --- |
| Example 37 | A3 | H7 | H27 | 5.7 | 3.9 |
| Example 38 | A3 | H26 | H26 | 5.1 | 3.5 |
| Example 39 | A7 | H26 | H26 | 6.4 | 3.6 |
| Example 40 | A26 | H25 | H18 | 6.2 | 4.0 |
| Example 41 | A37 | H10 | H21 | 6.1 | 3.9 |
| Example 42 | A38 | H25 | H26 | 5.2 | 3.6 |
| Example 43 | A39 | H18 | H18 | 6.1 | 3.8 |
| Example 44 | A46 | H18 | H19 | 6.1 | 4.0 |
| Example 45 | A47 | H26 | H26 | 5.7 | 3.5 |
| Example 46 | A48 | H18 | H18 | 5.9 | 3.9 |
| Example 47 | A52 | H26 | H26 | 5.7 | 3.5 |

The organic compound according to the invention is a compound which has a high quantum yield and exhibits light emission suitable for red light emission. Therefore, the use of the organic compound according to the invention as a constituent material of an organic light emitting device allows obtaining an organic light emitting device having good light emission properties.

The organic compound according to the invention can emit light in a red region by the basic skeleton itself.

Furthermore, the organic compound according to the invention exhibits red light emission with high color purity by the basic skeleton itself, and, therefore, can also provide an organic light emitting device with high luminous efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-267142, filed Dec. 6, 2011 and No. 2012-232175 filed Oct. 19, 2012, which is hereby incorporated by reference herein in its entirety.

The invention claimed is:

1. An organic compound represented by the following Formula (1),

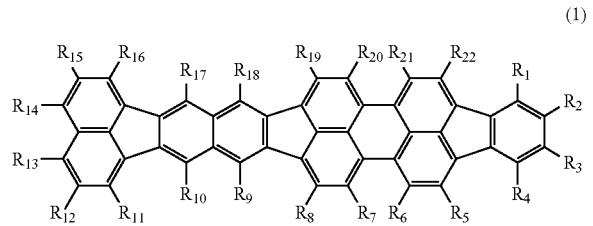

(1)

wherein, in Formula (1), $R_1$ to $R_{22}$ each are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein the $R_1$ to $R_{22}$ each are independently selected from the group consisting of a hydrogen atom, a halogen atom, a substituted or unsubstituted alkyl group, and a substituted or unsubstituted aryl group.

3. The organic compound according to claim 2, wherein $R_1$, $R_4$, $R_9$, $R_{10}$, $R_{17}$, and $R_{18}$ each are independently selected from the group consisting of a hydrogen atom, a substituted or unsubstituted alkyl group, and a substituted or unsubstituted aryl group and $R_2$, $R_3$, $R_{12}$, $R_{13}$, $R_{14}$, and $R_{15}$ each are independently selected from a hydrogen atom, a halogen atom, a substituted or unsubstituted alkyl group, and a substituted or unsubstituted aryl group.

4. An organic light emitting device, comprising:
an anode;
a cathode; and
at least one organic compound layer disposed between the anode and the cathode, wherein
the organic compound layer contains the organic compound according to claim 1.

5. The organic light emitting device according to claim 4, wherein at least one layer of the organic compound layers is a light emitting layer.

6. The organic light emitting device according to claim 5, which emits red light.

7. The organic light emitting device according to claim 6, further comprising another light emitting layer disposed while being laminated on the light emitting layer, wherein the other light emitting layer emits light of a different color from the color of the light emitted from the light emitting layer.

8. The organic light emitting device according to claim 7, which emits white light.

9. A display device, comprising:
a plurality of pixels, wherein
the plurality of pixels have the organic light emitting device according to claim 4 and a transistor connected to the organic light emitting device.

10. A display device, comprising:
a plurality of pixels, wherein
the plurality of pixels have the organic light emitting device according to claim 7, a transistor connected to the organic light emitting device, and a color filter.

11. An image display device, comprising:
an input portion for inputting image information; and
a display portion for outputting an image, wherein
the display portion has the display device according to claim 9.

12. A lighting device, comprising:
the organic light emitting device according to claim 4; and
an inverter circuit connected to the organic light emitting device.

13. The lighting device according to claim 12, further comprising a color filter.

14. An exposure light source, comprising a plurality of the organic light emitting devices according to claim 4 as light emitting points in one row.

15. An image formation device, comprising:
the exposure light source according to claim 14; and
a photoconductor drum which is exposed by light emitted from the exposure light source.

16. The organic light emitting device according to claim 4,
wherein the organic compound layer comprises a light emitting layer and an electron injection layer; and
wherein the electron injection layer contains the organic compound represented by the Formula (1).

17. A device comprising
an anode;
a cathode; and
at least one organic compound layer disposed between the anode and the cathode, wherein
the organic compound layer contains the organic compound according to claim 1.

* * * * *